United States Patent
Thome et al.

(10) Patent No.: US 9,051,595 B2
(45) Date of Patent: Jun. 9, 2015

(54) MALT1 SPECIFIC CLEAVAGE IN ASSAY AND SCREENING METHOD

(75) Inventors: Margot Thome, Mezieres (CH); Fabien Rebeaud, Epalinges (CH); Stephan Hailfinger, Lausanne (CH)

(73) Assignee: University of Lausanne, Lausanne (CH)

( * ) Notice: Subject to any disclaimer, the term of this patent is extended or adjusted under 35 U.S.C. 154(b) by 234 days.

(21) Appl. No.: 12/602,590

(22) PCT Filed: May 30, 2008

(86) PCT No.: PCT/IB2008/052122
§ 371 (c)(1),
(2), (4) Date: Dec. 22, 2009

(87) PCT Pub. No.: WO2008/146259
PCT Pub. Date: Dec. 4, 2008

(65) Prior Publication Data
US 2010/0184709 A1  Jul. 22, 2010

Related U.S. Application Data

(60) Provisional application No. 60/932,648, filed on Jun. 1, 2007.

(30) Foreign Application Priority Data

Jul. 11, 2007 (EP) .................. 07112228
Dec. 19, 2007 (EP) .................. 07123542

(51) Int. Cl.
*C12Q 1/37* (2006.01)
*G01N 31/22* (2006.01)

(52) U.S. Cl.
CPC ............ *C12Q 1/37* (2013.01); *C12Q 2521/537* (2013.01); *G01N 2500/02* (2013.01)

(58) Field of Classification Search
None
See application file for complete search history.

(56) References Cited

U.S. PATENT DOCUMENTS

2004/0023908 A1* 2/2004 Bennett et al. .................. 514/44
2004/0110145 A1  6/2004 Bennett et al.

FOREIGN PATENT DOCUMENTS

WO    WO0233058      4/2002
WO    WO 2006136951 A2 * 12/2006

OTHER PUBLICATIONS

Coornaert et al. T cell antigen receptor stimulation induces MALT1 paracaspase-mediated cleavage of the NF-KB inhibitor A20. Nature Immunology. Mar. 2008, vol. 9, No. 3, pp. 263-271.*
Lucas et al. Bc110 and MALT1, Independent Targets of Chromosomal Translocation . . . The Journal of Biological Chemistry. Jun. 1, 2001, vol. 276, No. 22, pp. 19012-19019.*
Snipas et al. Charateristics of the caspase-like catalytic domain of human paracaspase. Biological Chemistry. Nov. 2004, vol. 385, pp. 1093-1098.*
Sen et al. Inhibition of NH-kappaB Activation in Human T-Cell Lines by Anetholdithiolthione. Biochemical and Biophysical Research Communications. 1996, vol. 218, No. 1, pp. 148-153.*
Gosalia et al., "High Throughput Substrate Specificity Profiling of Serine and Cysteine Proteases Using Solution-phase Fluorogenic Peptide Microarrays", Molecular & Cellular Proteomics, vol. 4, May 1, 2005 pp. 626-636—XP009061144.
Database Geneseq Nov. 18, 2004—"Human protein sequence hCP41880", XP002450747.
Database UniProt Jul. 25, 2006 "B-cell CLL/lymphoma 10", XP002450748.
Rueda et al., "Bc110 Controls TCR- and FcgammaR-Induced Actin Polymerization", Journal of Immunology, vol. 178, No. 7, Apr. 1, 2007, pp. 4373-4384—XP002453187.
Misra et al., "Caspase-8 and c-FLIPL associate in Lipid Rafts with NF-kappa B adaptors during T Cell Activation", Journal of Biological Chemistry, vol. 282, No. 27, Apr. 26, 2007—XP002450744.
Uren et al., "Identification of Paracaspases and Metacaspases: Two Ancient Families of Caspase-like Proteins, One of which Plays a Key Role in MALT Lymphoma", Molecular Cell, Cell Press, vol. 6, No. 4, Oct. 2000, pp. 961-967—XP002207100.
Backes et al., "Synthesis of positional-scanning libraries of fluorogenic peptide substrate to define the extended substrate specificity of plasmin and thrombin", Nature Biotechnology, Nature Publishing Group, vol. 18, Feb. 1, 2000 pp. 187-193—XP002959316.
Rebeaud et al., "The proteolytic activity of the paracaspase MALT1 is key in T cell activation", Nature Immunology vol. 9, No. 3, Mar. 2008 pp. 272-281—XP002474047.

* cited by examiner

*Primary Examiner* — Jeffrey E Russel
(74) *Attorney, Agent, or Firm* — K&L Gates LLP

(57) ABSTRACT

The present invention is based on the surprising finding of a proteolytic cleavage function of human Malt1. More particularly, the present invention relates to enzyme and screening assays, methods for assessing cleaving activity, methods for screening, isolated polypeptides, antibodies and inhibitors of Malt1. The present invention also relates to the use of Malt1 as a proteolytic enzyme and the use of compounds comprising a peptide comprising an amino acid sequence according to any one of SEQ ID NO: 1-47 as substrates susceptible for specific proteolytic cleavage.

12 Claims, 10 Drawing Sheets

| | | |
|---|---|---|
| hBcl10 | ..FLPLRSR$_{228}$TVSRQ | SEQ ID NO: 76 |
| mBcl10 | ..FLPLRSR$_{228}$ALSRQ | SEQ ID NO: 77 |
| Atmc9 | ..AGVIKLR$_{351}$GLLMEEDE.. | SEQ ID NO: 78 |
| AtSerpin1 | ..NKTITSR$_{183}$ALPFKAVL.. | SEQ ID NO: 79 |
| mcII-Pa | ..HGAFESR$_{188}$GIHLPSRH.. | SEQ ID NO: 80 |
| mcII-Pa | ..KVKKFVK$_{269}$VLVTKLQS.. | SEQ ID NO: 81 |

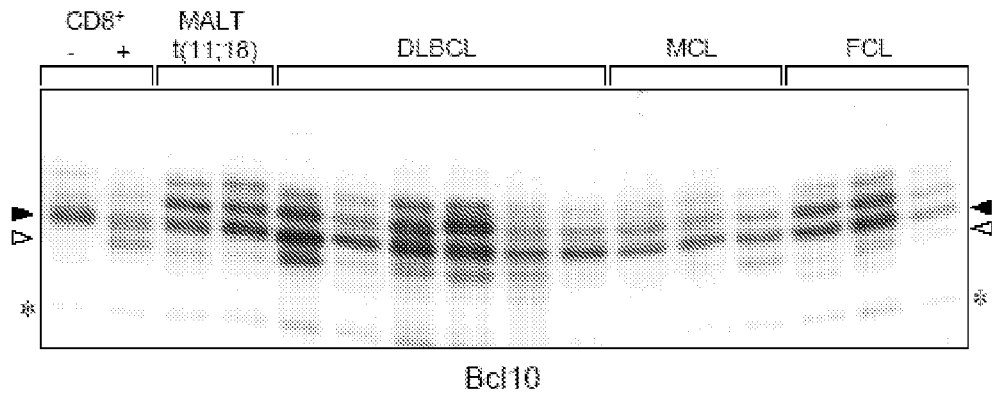

Figure 9

SEQ ID NO: 52   Bcl10 [Homo sapiens]   ANSSEMFLPLR$\underline{SR}_{228}$TVSRQ
SEQ ID NO: 53   Bcl10 [Mus musculus]   GNSSEMFLPLR$\underline{SR}_{228}$ALSRQ
SEQ ID NO: 54   A20 [Homo sapiens]    PEGLPGMALGA$\underline{SR}_{439}$GEAYE
SEQ ID NO: 2    Consensus:            $\underline{\text{S-R-}}$

Figure 10 A

SEQ ID NO: 55   Carma1 [Homo sapiens]   TNSFTKMQ$\underline{PPRSR}_{550}$SSIMS
SEQ ID NO: 56   Carma1 [Mus musculus]   TSSFSKMQ$\underline{PHRSR}_{562}$SSIMS
SEQ ID NO: 57   Carma1 [Bos taurus]     TNSFSKMQ$\underline{PHRSR}_{561}$SSIMS
SEQ ID NO: 58   Carma1 [H.s.] 2nd site  PFRPSVTS$\underline{VGHVR}_{653}$GPGPSSEQ ID
NO: 59          vE10 [viral, EHV-2]     PAPDPPSP$\underline{PLRTR}_{306}$RFFCC
(putative)

SEQ ID NO: 60   vE10 [viral, EHV-2]     QEVDDPSL$\underline{SVQGR}_{291}$GGPAP
SEQ ID NO: 61   MALT1 [Homo sapiens]   SNVTPADS$\underline{CHCSR}_{781}$TPDAF
(auto-processing)SEQ ID NO: 1  Consensus:        $\underline{\text{S/T/V/G-R-}}$

Figure 10 B

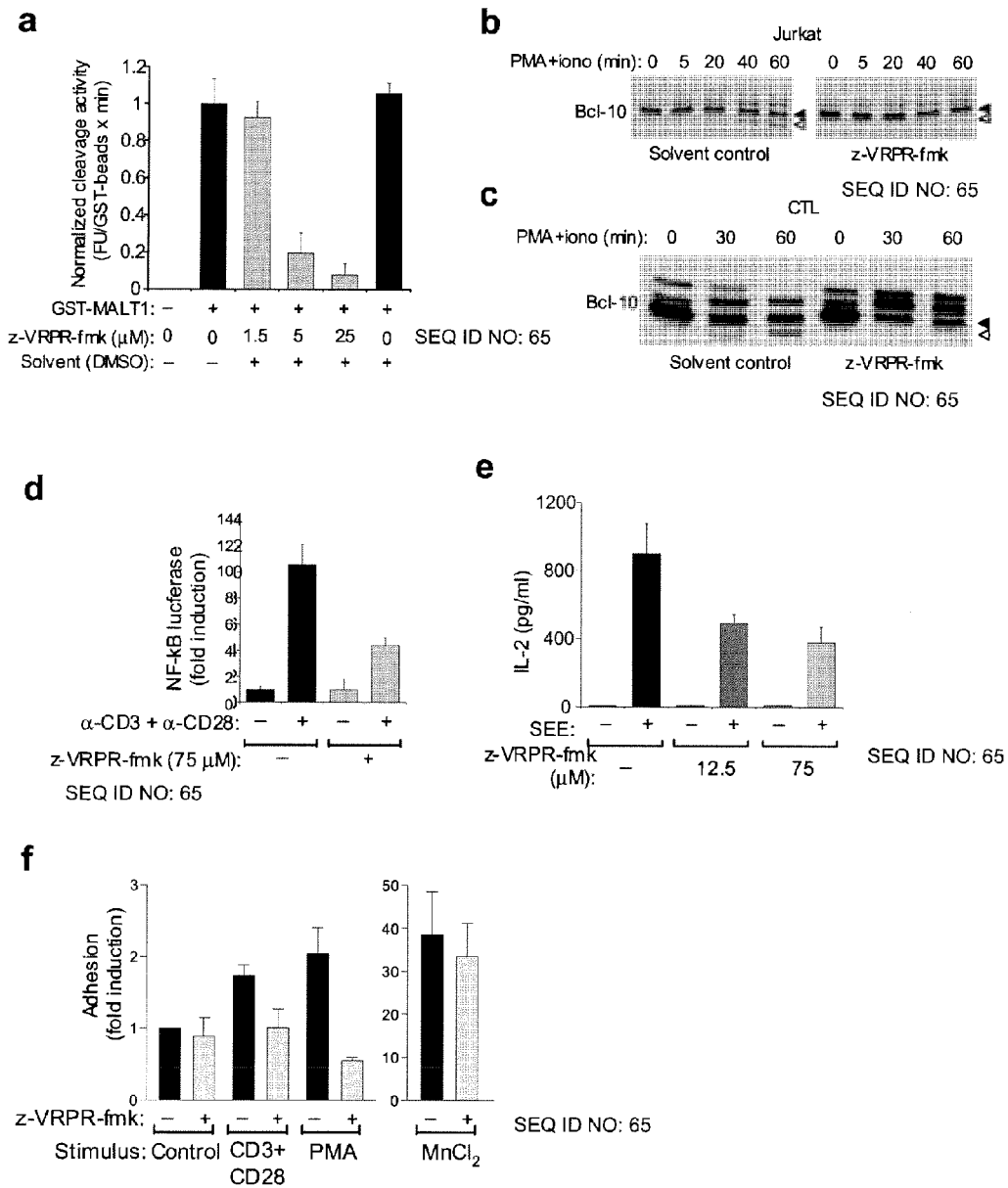
Figure 11 a-f

SEQUENCE LISTING

<160> NUMBER OF SEQ ID NOS: 82

<210> SEQ ID NO 1
<211> LENGTH: 2
<212> TYPE: PRT
<213> ORGANISM: Artificial
<220> FEATURE:
<223> OTHER INFORMATION: Consensus cleaving site 1 for MALT1 protease
      family
<220> FEATURE:
<221> NAME/KEY: misc_feature
<222> LOCATION: (1)..(1)
<223> OTHER INFORMATION: Xaa stands for any one selected from S, T, V,
      and G (Ser, Thr, Val, Gly)

<400> SEQUENCE: 1

Xaa Arg
1

<210> SEQ ID NO 2
<211> LENGTH: 2
<212> TYPE: PRT
<213> ORGANISM: Homo sapiens

<400> SEQUENCE: 2

Ser Arg
1

<210> SEQ ID NO 3
<211> LENGTH: 2
<212> TYPE: PRT
<213> ORGANISM: Equine herpesvirus 2

<400> SEQUENCE: 3

Thr Arg
1

<210> SEQ ID NO 4
<211> LENGTH: 3
<212> TYPE: PRT
<213> ORGANISM: Homo sapiens

<400> SEQUENCE: 4

Arg Ser Arg
1

<210> SEQ ID NO 5
<211> LENGTH: 3
<212> TYPE: PRT
<213> ORGANISM: Equine herpesvirus 2

<400> SEQUENCE: 5

Arg Thr Arg
1

<210> SEQ ID NO 6
<211> LENGTH: 5
<212> TYPE: PRT
<213> ORGANISM: Artificial
<220> FEATURE:
<223> OTHER INFORMATION: Consensus cleaving site 6 for MALT1 protease
      family
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 6

Pro Xaa Arg Ser Arg
1               5

<210> SEQ ID NO 7
<211> LENGTH: 5
<212> TYPE: PRT
<213> ORGANISM: Artificial
<220> FEATURE:
<223> OTHER INFORMATION: Consensus cleaving site 7 for MALT1 protease
      family
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 7

Pro Xaa Arg Thr Arg
1               5

<210> SEQ ID NO 8
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 8

Gly Arg Ser Arg
1

<210> SEQ ID NO 9
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 9

Ala Arg Ser Arg
1

<210> SEQ ID NO 10
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 10

Val Arg Ser Arg
1

<210> SEQ ID NO 11
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 11

Leu Arg Ser Arg
1

<210> SEQ ID NO 12
<211> LENGTH: 4
<212> TYPE: PRT
<213> ORGANISM: Artificial

```
<220> FEATURE:
<223> OTHER INFORMATION: Exemplary target cleaving site for hMalt1

<400> SEQUENCE: 12

Ile Arg Ser Arg
1

<210> SEQ ID NO 13
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 13

Pro Arg Ser Arg
1

<210> SEQ ID NO 14
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 14

Phe Arg Ser Arg
1

<210> SEQ ID NO 15
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 15

Tyr Arg Ser Arg
1

<210> SEQ ID NO 16
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 16

Trp Arg Ser Arg
1

<210> SEQ ID NO 17
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 17

Cys Arg Ser Arg
1

<210> SEQ ID NO 18
<211> LENGTH: 4
<212> TYPE: PRT
<213> ORGANISM: Artificial
<220> FEATURE:
```

<223> OTHER INFORMATION: Exemplary target cleaving site for hMalt1

<400> SEQUENCE: 18

Met Arg Ser Arg
1

<210> SEQ ID NO 19
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 19

Ser Arg Ser Arg
1

<210> SEQ ID NO 20
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 20

Thr Arg Ser Arg
1

<210> SEQ ID NO 21
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 21

Lys Arg Ser Arg
1

<210> SEQ ID NO 22
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 22

Arg Arg Ser Arg
1

<210> SEQ ID NO 23
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 23

His Arg Ser Arg
1

<210> SEQ ID NO 24
<211> LENGTH: 4
<212> TYPE: PRT
<213> ORGANISM: Artificial
<220> FEATURE:
<223> OTHER INFORMATION: Exemplary target cleaving site for hMalt1

```
<400> SEQUENCE: 24

Asp Arg Ser Arg
1

<210> SEQ ID NO 25
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 25

Glu Arg Ser Arg
1

<210> SEQ ID NO 26
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 26

Asn Arg Ser Arg
1

<210> SEQ ID NO 27
<211> LENGTH: 4
<212> TYPE: PRT
<213> ORGANISM: Artificial
<220> FEATURE:
<223> OTHER INFORMATION: Exemplary target cleaving site for hMalt1

<400> SEQUENCE: 27

Gln Arg Ser Arg
1

<210> SEQ ID NO 28
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 28

Gly Arg Thr Arg
1

<210> SEQ ID NO 29
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 29

Ala Arg Thr Arg
1

<210> SEQ ID NO 30
<211> LENGTH: 4
<212> TYPE: PRT
<213> ORGANISM: Artificial
<220> FEATURE:
<223> OTHER INFORMATION: Target cleaving site for hMalt1
```

```
<400> SEQUENCE: 30

Val Arg Thr Arg
1

<210> SEQ ID NO 31
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 31

Leu Arg Thr Arg
1

<210> SEQ ID NO 32
<211> LENGTH: 5
<212> TYPE: PRT
<213> ORGANISM: Artificial
<220> FEATURE:
<223> OTHER INFORMATION: Target cleaving site for hMalt1

<400> SEQUENCE: 32

Pro Ile Arg Thr Arg
1               5

<210> SEQ ID NO 33
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 33

Pro Arg Thr Arg
1

<210> SEQ ID NO 34
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 34

Phe Arg Thr Arg
1

<210> SEQ ID NO 35
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 35

Tyr Arg Thr Arg
1

<210> SEQ ID NO 36
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 36
```

Trp Arg Thr Arg
1

<210> SEQ ID NO 37
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 37

Cys Arg Thr Arg
1

<210> SEQ ID NO 38
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 38

Met Arg Thr Arg
1

<210> SEQ ID NO 39
<211> LENGTH: 5
<212> TYPE: PRT
<213> ORGANISM: Artificial
<220> FEATURE:
<223> OTHER INFORMATION: Target cleaving site for hMalt1

<400> SEQUENCE: 39

Pro Ser Arg Thr Arg
1               5

<210> SEQ ID NO 40
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 40

Thr Arg Thr Arg
1

<210> SEQ ID NO 41
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 41

Lys Arg Thr Arg
1

<210> SEQ ID NO 42
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 42

Arg Arg Thr Arg
1

<210> SEQ ID NO 43
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 43

His Arg Thr Arg
1

<210> SEQ ID NO 44
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 44

Asp Arg Thr Arg
1

<210> SEQ ID NO 45
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 45

Glu Arg Thr Arg
1

<210> SEQ ID NO 46
<211> LENGTH: 5
<212> TYPE: PRT
<213> ORGANISM: Artificial
<220> FEATURE:
<223> OTHER INFORMATION: Target cleaving site for hMalt1

<400> SEQUENCE: 46

Pro Asn Arg Thr Arg
1               5

<210> SEQ ID NO 47
<211> LENGTH: 4
<212> TYPE: PRT
<213> ORGANISM: Artificial
<220> FEATURE:
<223> OTHER INFORMATION: Target cleaving site for hMalt1

<400> SEQUENCE: 47

Gln Arg Thr Arg
1

<210> SEQ ID NO 48
<211> LENGTH: 824
<212> TYPE: PRT
<213> ORGANISM: Homo sapiens

<400> SEQUENCE: 48

Met Ser Leu Leu Gly Asp Pro Leu Gln Ala Leu Pro Pro Ser Ala Ala
1               5                   10                  15

```
Pro Thr Gly Pro Leu Leu Ala Pro Ala Gly Ala Thr Leu Asn Arg
             20                  25                  30

Leu Arg Glu Pro Leu Leu Arg Arg Leu Ser Glu Leu Leu Asp Gln Ala
         35                  40                  45

Pro Glu Gly Arg Gly Trp Arg Arg Leu Ala Glu Leu Ala Gly Ser Arg
     50                  55                  60

Gly Arg Leu Arg Leu Ser Cys Leu Asp Leu Glu Gln Cys Ser Leu Lys
 65              70                  75                  80

Val Leu Glu Pro Glu Gly Ser Pro Ser Leu Cys Leu Leu Lys Leu Met
                 85                  90                  95

Gly Glu Lys Gly Cys Thr Val Thr Glu Leu Ser Asp Phe Leu Gln Ala
             100                 105                 110

Met Glu His Thr Glu Val Leu Gln Leu Leu Ser Pro Gly Ile Lys
         115                 120                 125

Ile Thr Val Asn Pro Glu Ser Lys Ala Val Leu Ala Gly Gln Phe Val
    130                 135                 140

Lys Leu Cys Cys Arg Ala Thr Gly His Pro Phe Val Gln Tyr Gln Trp
145                 150                 155                 160

Phe Lys Met Asn Lys Glu Ile Pro Asn Gly Asn Thr Ser Glu Leu Ile
                165                 170                 175

Phe Asn Ala Val His Val Lys Asp Ala Gly Phe Tyr Val Cys Arg Val
            180                 185                 190

Asn Asn Asn Phe Thr Phe Glu Phe Ser Gln Trp Ser Gln Leu Asp Val
        195                 200                 205

Cys Asp Ile Pro Glu Ser Phe Gln Arg Ser Val Asp Gly Val Ser Glu
    210                 215                 220

Ser Lys Leu Gln Ile Cys Val Glu Pro Thr Ser Gln Lys Leu Met Pro
225                 230                 235                 240

Gly Ser Thr Leu Val Leu Gln Cys Val Ala Val Gly Ser Pro Ile Pro
                245                 250                 255

His Tyr Gln Trp Phe Lys Asn Glu Leu Pro Leu Thr His Glu Thr Lys
            260                 265                 270

Lys Leu Tyr Met Val Pro Tyr Val Asp Leu Glu His Gln Gly Thr Tyr
        275                 280                 285

Trp Cys His Val Tyr Asn Asp Arg Asp Ser Gln Asp Ser Lys Lys Val
    290                 295                 300

Glu Ile Ile Ile Gly Arg Thr Asp Glu Ala Val Glu Cys Thr Glu Asp
305                 310                 315                 320

Glu Leu Asn Asn Leu Gly His Pro Asp Asn Lys Glu Gln Thr Thr Asp
                325                 330                 335

Gln Pro Leu Ala Lys Asp Lys Val Ala Leu Leu Ile Gly Asn Met Asn
            340                 345                 350

Tyr Arg Glu His Pro Lys Leu Lys Ala Pro Leu Val Asp Val Tyr Glu
        355                 360                 365

Leu Thr Asn Leu Leu Arg Gln Leu Asp Phe Lys Val Val Ser Leu Leu
    370                 375                 380

Asp Leu Thr Glu Tyr Glu Met Arg Asn Ala Val Asp Glu Phe Leu Leu
385                 390                 395                 400

Leu Leu Asp Lys Gly Val Tyr Gly Leu Leu Tyr Tyr Ala Gly His Gly
                405                 410                 415

Tyr Glu Asn Phe Gly Asn Ser Phe Met Val Pro Val Asp Ala Pro Asn
            420                 425                 430

Pro Tyr Arg Ser Glu Asn Cys Leu Cys Val Gln Asn Ile Leu Lys Leu
```

-continued

```
                    435                 440                 445
Met Gln Glu Lys Glu Thr Gly Leu Asn Val Phe Leu Leu Asp Met Cys
    450                 455                 460

Arg Lys Arg Asn Asp Tyr Asp Asp Thr Ile Pro Ile Leu Asp Ala Leu
465                 470                 475                 480

Lys Val Thr Ala Asn Ile Val Phe Gly Tyr Ala Thr Cys Gln Gly Ala
                485                 490                 495

Glu Ala Phe Glu Ile Gln His Ser Gly Leu Ala Asn Gly Ile Phe Met
            500                 505                 510

Lys Phe Leu Lys Asp Arg Leu Leu Glu Asp Lys Lys Ile Thr Val Leu
        515                 520                 525

Leu Asp Glu Val Ala Glu Asp Met Gly Lys Cys His Leu Thr Lys Gly
    530                 535                 540

Lys Gln Ala Leu Glu Ile Arg Ser Ser Leu Ser Glu Lys Arg Ala Leu
545                 550                 555                 560

Thr Asp Pro Ile Gln Gly Thr Glu Tyr Ser Ala Glu Ser Leu Val Arg
                565                 570                 575

Asn Leu Gln Trp Ala Lys Ala His Glu Leu Pro Glu Ser Met Cys Leu
            580                 585                 590

Lys Phe Asp Cys Gly Val Gln Ile Gln Leu Gly Phe Ala Ala Glu Phe
        595                 600                 605

Ser Asn Val Met Ile Ile Tyr Thr Ser Ile Val Tyr Lys Pro Pro Glu
    610                 615                 620

Ile Ile Met Cys Asp Ala Tyr Val Thr Asp Phe Pro Leu Asp Leu Asp
625                 630                 635                 640

Ile Asp Pro Lys Asp Ala Asn Lys Gly Thr Pro Glu Thr Gly Ser
                645                 650                 655

Tyr Leu Val Ser Lys Asp Leu Pro Lys His Cys Leu Tyr Thr Arg Leu
            660                 665                 670

Ser Ser Leu Gln Lys Leu Lys Glu His Leu Val Phe Thr Val Cys Leu
        675                 680                 685

Ser Tyr Gln Tyr Ser Gly Leu Glu Asp Thr Val Glu Asp Lys Gln Glu
    690                 695                 700

Val Asn Val Gly Lys Pro Leu Ile Ala Lys Leu Asp Met His Arg Gly
705                 710                 715                 720

Leu Gly Arg Lys Thr Cys Phe Gln Thr Cys Leu Met Ser Asn Gly Pro
                725                 730                 735

Tyr Gln Ser Ser Ala Ala Thr Ser Gly Gly Ala Gly His Tyr His Ser
            740                 745                 750

Leu Gln Asp Pro Phe His Gly Val Tyr His Ser His Pro Gly Asn Pro
        755                 760                 765

Ser Asn Val Thr Pro Ala Asp Ser Cys His Cys Ser Arg Thr Pro Asp
    770                 775                 780

Ala Phe Ile Ser Ser Phe Ala His His Ala Ser Cys His Phe Ser Arg
785                 790                 795                 800

Ser Asn Val Pro Val Glu Thr Thr Asp Glu Ile Pro Phe Ser Phe Ser
                805                 810                 815

Asp Arg Leu Arg Ile Ser Glu Lys
            820

<210> SEQ ID NO 49
<211> LENGTH: 5
<212> TYPE: PRT
<213> ORGANISM: Homo sapiens
```

```
<400> SEQUENCE: 49

Thr Val Ser Arg Gln
1               5

<210> SEQ ID NO 50
<211> LENGTH: 228
<212> TYPE: PRT
<213> ORGANISM: Homo sapiens

<400> SEQUENCE: 50

Met Glu Pro Thr Ala Pro Ser Leu Thr Glu Glu Asp Leu Thr Glu Val
1               5                   10                  15

Lys Lys Asp Ala Leu Glu Asn Leu Arg Val Tyr Leu Cys Glu Lys Ile
                20                  25                  30

Ile Ala Glu Arg His Phe Asp His Leu Arg Ala Lys Lys Ile Leu Ser
            35                  40                  45

Arg Glu Asp Thr Glu Glu Ile Ser Cys Arg Thr Ser Ser Arg Lys Arg
    50                  55                  60

Ala Gly Lys Leu Leu Asp Tyr Leu Gln Glu Asn Pro Lys Gly Leu Asp
65                  70                  75                  80

Thr Leu Val Glu Ser Ile Arg Arg Glu Lys Thr Gln Asn Phe Leu Ile
                85                  90                  95

Gln Lys Ile Thr Asp Glu Val Leu Lys Leu Arg Asn Ile Lys Leu Glu
                100                 105                 110

His Leu Lys Gly Leu Lys Cys Ser Ser Cys Glu Pro Phe Pro Asp Gly
            115                 120                 125

Ala Thr Asn Asn Leu Ser Arg Ser Asn Ser Asp Glu Ser Asn Phe Ser
    130                 135                 140

Glu Lys Leu Arg Ala Ser Thr Val Met Tyr His Pro Glu Gly Glu Ser
145                 150                 155                 160

Ser Thr Thr Pro Phe Phe Ser Thr Asn Ser Ser Leu Asn Leu Pro Val
                165                 170                 175

Leu Glu Val Gly Arg Thr Glu Asn Thr Ile Phe Ser Ser Thr Thr Leu
                180                 185                 190

Pro Arg Pro Gly Asp Pro Gly Ala Pro Pro Leu Pro Asp Leu Gln
            195                 200                 205

Leu Glu Glu Gly Thr Cys Ala Asn Ser Ser Glu Met Phe Leu Pro
    210                 215                 220

Leu Arg Ser Arg
225

<210> SEQ ID NO 51
<211> LENGTH: 1147
<212> TYPE: PRT
<213> ORGANISM: Homo sapiens
<300> PUBLICATION INFORMATION:
<308> DATABASE ACCESSION NUMBER: AAL34460
<309> DATABASE ENTRY DATE: 2001-11-22
<313> RELEVANT RESIDUES IN SEQ ID NO: (1)..(1147)

<400> SEQUENCE: 51

Met Asp Asp Tyr Met Glu Thr Leu Lys Asp Glu Glu Asp Ala Leu Trp
1               5                   10                  15

Glu Asn Val Glu Cys Asn Arg His Met Leu Ser Arg Tyr Ile Asn Pro
                20                  25                  30

Ala Lys Leu Thr Pro Tyr Leu Arg Gln Cys Lys Val Ile Asp Glu Gln
            35                  40                  45
```

```
Asp Glu Asp Glu Val Leu Asn Ala Pro Met Leu Pro Ser Lys Ile Asn
    50                      55                      60

Arg Ala Gly Arg Leu Leu Asp Ile Leu His Thr Lys Gly Gln Arg Gly
65                      70                      75                      80

Tyr Val Val Phe Leu Glu Ser Leu Glu Phe Tyr Tyr Pro Glu Leu Tyr
                    85                      90                      95

Lys Leu Val Thr Gly Lys Glu Pro Thr Arg Arg Phe Ser Thr Ile Val
                100                     105                     110

Val Glu Glu Gly His Glu Gly Leu Thr His Phe Leu Met Asn Glu Val
            115                     120                     125

Ile Lys Leu Gln Gln Gln Met Lys Ala Lys Asp Leu Gln Arg Cys Glu
    130                     135                     140

Leu Leu Ala Arg Leu Arg Gln Leu Glu Asp Glu Lys Lys Gln Met Thr
145                     150                     155                     160

Leu Thr Arg Val Glu Leu Leu Thr Phe Gln Glu Arg Tyr Tyr Lys Met
                    165                     170                     175

Lys Glu Glu Arg Asp Ser Tyr Asn Asp Glu Leu Val Lys Val Lys Asp
                180                     185                     190

Asp Asn Tyr Asn Leu Ala Met Arg Tyr Ala Gln Leu Ser Glu Glu Lys
            195                     200                     205

Asn Met Ala Val Met Arg Ser Arg Asp Leu Gln Leu Glu Ile Asp Gln
    210                     215                     220

Leu Lys His Arg Leu Asn Lys Met Glu Glu Glu Cys Lys Leu Glu Arg
225                     230                     235                     240

Asn Gln Ser Leu Lys Leu Lys Asn Asp Ile Glu Asn Arg Pro Lys Lys
                    245                     250                     255

Glu Gln Val Leu Glu Leu Glu Arg Glu Asn Glu Met Leu Lys Thr Lys
                260                     265                     270

Asn Gln Glu Leu Gln Ser Ile Ile Gln Ala Gly Lys Arg Ser Leu Pro
            275                     280                     285

Asp Ser Asp Lys Ala Ile Leu Asp Ile Leu Glu His Asp Arg Lys Glu
    290                     295                     300

Ala Leu Glu Asp Arg Gln Glu Leu Val Asn Arg Ile Tyr Asn Leu Gln
305                     310                     315                     320

Glu Glu Ala Arg Gln Ala Glu Glu Leu Arg Asp Lys Tyr Leu Glu Glu
                    325                     330                     335

Lys Glu Asp Leu Glu Leu Lys Cys Ser Thr Leu Gly Lys Asp Cys Glu
                340                     345                     350

Met Tyr Lys His Arg Met Asn Thr Val Met Leu Gln Leu Glu Glu Val
            355                     360                     365

Glu Arg Glu Arg Asp Gln Ala Phe His Ser Arg Asp Glu Ala Gln Thr
    370                     375                     380

Gln Tyr Ser Gln Cys Leu Ile Glu Lys Asp Lys Tyr Arg Lys Gln Ile
385                     390                     395                     400

Arg Glu Leu Glu Glu Lys Asn Asp Glu Met Arg Ile Glu Met Val Arg
                    405                     410                     415

Arg Glu Ala Cys Ile Val Asn Leu Glu Ser Lys Leu Arg Arg Leu Ser
                420                     425                     430

Lys Asp Ser Asn Asn Leu Asp Gln Ser Leu Pro Arg Asn Leu Pro Val
            435                     440                     445

Thr Ile Ile Ser Gln Asp Phe Gly Asp Ala Ser Pro Arg Thr Asn Gly
    450                     455                     460
```

```
Gln Glu Ala Asp Asp Ser Ser Thr Ser Glu Ser Pro Glu Asp Ser
465                 470                 475                 480

Lys Tyr Phe Leu Pro Tyr His Pro Pro Gln Arg Arg Met Asn Leu Lys
            485                 490                 495

Gly Ile Gln Leu Gln Arg Ala Lys Ser Pro Ile Ser Leu Lys Arg Thr
        500                 505                 510

Ser Asp Phe Gln Ala Lys Gly His Glu Glu Glu Gly Thr Asp Ala Ser
        515                 520                 525

Pro Ser Ser Cys Gly Ser Leu Pro Ile Thr Asn Ser Phe Thr Lys Met
    530                 535                 540

Gln Pro Pro Arg Ser Arg Ser Ser Ile Met Ser Ile Thr Ala Glu Pro
545                 550                 555                 560

Pro Gly Asn Asp Ser Ile Val Arg Arg Tyr Lys Glu Asp Ala Pro His
                565                 570                 575

Arg Ser Thr Val Glu Glu Asp Asn Asp Ser Gly Gly Phe Asp Ala Leu
            580                 585                 590

Asp Leu Asp Asp Asp Ser His Glu Arg Tyr Ser Phe Gly Pro Ser Ser
        595                 600                 605

Ile His Ser Ser Ser Ser Ser His Gln Ser Glu Gly Leu Asp Ala Tyr
    610                 615                 620

Asp Leu Glu Gln Val Asn Leu Met Phe Arg Lys Phe Ser Leu Glu Arg
625                 630                 635                 640

Pro Phe Arg Pro Ser Val Thr Ser Val Gly His Val Arg Gly Pro Gly
                645                 650                 655

Pro Ser Val Gln His Thr Thr Leu Asn Gly Asp Ser Leu Thr Ser Gln
            660                 665                 670

Leu Thr Leu Leu Gly Gly Asn Ala Arg Gly Ser Phe Val His Ser Val
        675                 680                 685

Lys Pro Gly Ser Leu Ala Glu Lys Ala Gly Leu Arg Glu Gly His Gln
    690                 695                 700

Leu Leu Leu Leu Glu Gly Cys Ile Arg Gly Glu Arg Gln Ser Val Pro
705                 710                 715                 720

Leu Asp Thr Cys Thr Lys Glu Glu Ala His Trp Thr Ile Gln Arg Cys
                725                 730                 735

Ser Gly Pro Val Thr Leu His Tyr Lys Val Asn His Glu Gly Tyr Arg
            740                 745                 750

Lys Leu Val Lys Asp Met Glu Asp Gly Leu Ile Thr Ser Gly Asp Ser
        755                 760                 765

Phe Tyr Ile Arg Leu Asn Leu Asn Ile Ser Ser Gln Leu Asp Ala Cys
    770                 775                 780

Thr Met Ser Leu Lys Cys Asp Asp Val Val His Val Arg Asp Thr Met
785                 790                 795                 800

Tyr Gln Asp Arg His Glu Trp Leu Cys Ala Arg Val Asp Pro Phe Thr
                805                 810                 815

Asp His Asp Leu Asp Met Gly Thr Ile Pro Ser Tyr Ser Arg Ala Gln
            820                 825                 830

Gln Leu Leu Leu Val Lys Leu Gln Arg Leu Met His Arg Gly Ser Arg
        835                 840                 845

Glu Glu Val Asp Gly Thr His His Thr Leu Arg Ala Leu Arg Asn Thr
    850                 855                 860

Leu Gln Pro Glu Glu Ala Leu Ser Thr Ser Asp Pro Arg Val Ser Pro
865                 870                 875                 880

Arg Leu Ser Arg Ala Ser Phe Leu Phe Gly Gln Leu Leu Gln Phe Val
```

```
                        885                 890                 895
Ser Arg Ser Glu Asn Lys Tyr Lys Arg Met Asn Ser Asn Glu Arg Val
            900                 905                 910

Arg Ile Ile Ser Gly Ser Pro Leu Gly Ser Leu Ala Arg Ser Ser Leu
            915                 920                 925

Asp Ala Thr Lys Leu Leu Thr Glu Lys Gln Glu Leu Asp Pro Glu
            930                 935                 940

Ser Glu Leu Gly Lys Asn Leu Ser Leu Ile Pro Tyr Ser Leu Val Arg
945                 950                 955                 960

Ala Phe Tyr Cys Glu Arg Arg Pro Val Leu Phe Thr Pro Thr Val
            965                 970                 975

Leu Ala Lys Thr Leu Val Gln Arg Leu Leu Asn Ser Gly Gly Ala Met
            980                 985                 990

Glu Phe Thr Ile Cys Lys Ser Asp Ile Val Thr Arg Asp Glu Phe Leu
            995                 1000                1005

Arg Arg Gln Lys Thr Glu Thr Ile Ile Tyr Ser Arg Glu Lys Asn
    1010                1015                1020

Pro Asn Ala Phe Glu Cys Ile Ala Pro Ala Asn Ile Glu Ala Val
    1025                1030                1035

Ala Ala Lys Asn Lys His Cys Leu Leu Glu Ala Gly Ile Gly Cys
    1040                1045                1050

Thr Arg Asp Leu Ile Lys Ser Asn Ile Tyr Pro Ile Val Leu Phe
    1055                1060                1065

Ile Arg Val Cys Glu Lys Asn Ile Lys Arg Phe Arg Lys Leu Leu
    1070                1075                1080

Pro Arg Pro Glu Thr Glu Glu Glu Phe Leu Arg Val Cys Arg Leu
    1085                1090                1095

Lys Glu Lys Glu Leu Glu Ala Leu Pro Cys Leu Tyr Ala Thr Val
    1100                1105                1110

Glu Pro Asp Met Trp Gly Ser Val Glu Glu Leu Leu Arg Val Val
    1115                1120                1125

Lys Asp Lys Ile Gly Glu Glu Gln Arg Lys Thr Ile Trp Val Asp
    1130                1135                1140

Glu Asp Gln Leu
    1145

<210> SEQ ID NO 52
<211> LENGTH: 18
<212> TYPE: PRT
<213> ORGANISM: Homo sapiens

<400> SEQUENCE: 52

Ala Asn Ser Ser Glu Met Phe Leu Pro Leu Arg Ser Arg Thr Val Ser
1               5                   10                  15

Arg Gln

<210> SEQ ID NO 53
<211> LENGTH: 18
<212> TYPE: PRT
<213> ORGANISM: Mus musculus

<400> SEQUENCE: 53

Gly Asn Ser Ser Glu Met Phe Leu Pro Leu Arg Ser Arg Ala Leu Ser
1               5                   10                  15

Arg Gln
```

<210> SEQ ID NO 54
<211> LENGTH: 18
<212> TYPE: PRT
<213> ORGANISM: Homo sapiens

<400> SEQUENCE: 54

Pro Glu Gly Leu Pro Gly Met Ala Leu Gly Ala Ser Arg Gly Glu Ala
1               5                   10                  15

Tyr Glu

<210> SEQ ID NO 55
<211> LENGTH: 18
<212> TYPE: PRT
<213> ORGANISM: Homo sapiens

<400> SEQUENCE: 55

Thr Asn Ser Phe Thr Lys Met Gln Pro Pro Arg Ser Arg Ser Ser Ile
1               5                   10                  15

Met Ser

<210> SEQ ID NO 56
<211> LENGTH: 18
<212> TYPE: PRT
<213> ORGANISM: Mus musculus

<400> SEQUENCE: 56

Thr Ser Ser Phe Ser Lys Met Gln Pro His Arg Ser Arg Ser Ser Ile
1               5                   10                  15

Met Ser

<210> SEQ ID NO 57
<211> LENGTH: 18
<212> TYPE: PRT
<213> ORGANISM: Bos taurus

<400> SEQUENCE: 57

Thr Asn Ser Phe Ser Lys Met Gln Pro His Arg Ser Arg Ser Ser Ile
1               5                   10                  15

Met Ser

<210> SEQ ID NO 58
<211> LENGTH: 18
<212> TYPE: PRT
<213> ORGANISM: Homo sapiens

<400> SEQUENCE: 58

Pro Phe Arg Pro Ser Val Thr Ser Val Gly His Val Arg Gly Pro Gly
1               5                   10                  15

Pro Ser

<210> SEQ ID NO 59
<211> LENGTH: 18
<212> TYPE: PRT
<213> ORGANISM: Equine herpesvirus

<400> SEQUENCE: 59

Pro Ala Pro Asp Pro Pro Ser Pro Pro Leu Arg Thr Arg Arg Phe Phe
1               5                   10                  15

Cys Cys

```
<210> SEQ ID NO 60
<211> LENGTH: 18
<212> TYPE: PRT
<213> ORGANISM: Equine herpesvirus

<400> SEQUENCE: 60

Gln Glu Val Asp Asp Pro Ser Leu Ser Val Gln Gly Arg Gly Gly Pro
1               5                   10                  15
Ala Pro

<210> SEQ ID NO 61
<211> LENGTH: 18
<212> TYPE: PRT
<213> ORGANISM: H. sapiens

<400> SEQUENCE: 61

Ser Asn Val Thr Pro Ala Asp Ser Cys His Cys Ser Arg Thr Pro Asp
1               5                   10                  15
Ala Phe

<210> SEQ ID NO 62
<211> LENGTH: 18
<212> TYPE: PRT
<213> ORGANISM: Rattus norvegicus

<400> SEQUENCE: 62

Gly Asn Ser Ser Glu Met Phe Leu Pro Leu Arg Ser Arg Ala Leu Ser
1               5                   10                  15
Arg Gln

<210> SEQ ID NO 63
<211> LENGTH: 18
<212> TYPE: PRT
<213> ORGANISM: Bos taurus

<400> SEQUENCE: 63

Gly Asn Ser Ser Glu Met Phe Leu Pro Leu Arg Ser Arg Ala Val Leu
1               5                   10                  15
Arg Gln

<210> SEQ ID NO 64
<211> LENGTH: 18
<212> TYPE: PRT
<213> ORGANISM: Canis familiaris

<400> SEQUENCE: 64

Thr Asn Ser Phe Ser Lys Met Gln Pro His Arg Ser Arg Ser Ser Ile
1               5                   10                  15
Met Ser

<210> SEQ ID NO 65
<211> LENGTH: 4
<212> TYPE: PRT
<213> ORGANISM: Artificial
<220> FEATURE:
<223> OTHER INFORMATION: Tetrapeptide sequence of Malt1 inhibitor

<400> SEQUENCE: 65

Val Arg Pro Arg
1

<210> SEQ ID NO 66
```

```
<211> LENGTH: 5
<212> TYPE: PRT
<213> ORGANISM: Artificial
<220> FEATURE:
<223> OTHER INFORMATION: Exemplary target sequence site for Malt1

<400> SEQUENCE: 66

Pro Gly Arg Ser Arg
1               5

<210> SEQ ID NO 67
<211> LENGTH: 5
<212> TYPE: PRT
<213> ORGANISM: Artificial
<220> FEATURE:
<223> OTHER INFORMATION: Exemplary target cleaving site for hMalt1

<400> SEQUENCE: 67

Pro Ala Arg Ser Arg
1               5

<210> SEQ ID NO 68
<211> LENGTH: 5
<212> TYPE: PRT
<213> ORGANISM: Artificial
<220> FEATURE:
<223> OTHER INFORMATION: Exemplary target cleaving site for hMalt1

<400> SEQUENCE: 68

Pro Leu Arg Ser Arg
1               5

<210> SEQ ID NO 69
<211> LENGTH: 5
<212> TYPE: PRT
<213> ORGANISM: Artificial
<220> FEATURE:
<223> OTHER INFORMATION: Exemplary target cleaving site for hMalt1

<400> SEQUENCE: 69

Pro His Arg Ser Arg
1               5

<210> SEQ ID NO 70
<211> LENGTH: 5
<212> TYPE: PRT
<213> ORGANISM: Artificial
<220> FEATURE:
<223> OTHER INFORMATION: Exemplary target cleaving site for hMalt1

<400> SEQUENCE: 70

Pro Pro Arg Ser Arg
1               5

<210> SEQ ID NO 71
<211> LENGTH: 5
<212> TYPE: PRT
<213> ORGANISM: Artificial
<220> FEATURE:
<223> OTHER INFORMATION: Exemplary target cleaving site for hMalt1

<400> SEQUENCE: 71

Pro Leu Arg Thr Arg
1               5

<210> SEQ ID NO 72
<211> LENGTH: 5
```

```
<212> TYPE: PRT
<213> ORGANISM: Artificial
<220> FEATURE:
<223> OTHER INFORMATION: Exemplary target cleaving site for hMalt1

<400> SEQUENCE: 72

Pro His Arg Thr Arg
1               5

<210> SEQ ID NO 73
<211> LENGTH: 5
<212> TYPE: PRT
<213> ORGANISM: Artificial
<220> FEATURE:
<223> OTHER INFORMATION: Exemplary target cleaving site for hMalt1

<400> SEQUENCE: 73

Pro Pro Arg Thr Arg
1               5

<210> SEQ ID NO 74
<211> LENGTH: 9
<212> TYPE: PRT
<213> ORGANISM: Artificial
<220> FEATURE:
<223> OTHER INFORMATION: Label for peptide

<400> SEQUENCE: 74

Asn Leu Val Pro Met Val Ala Thr Val
1               5

<210> SEQ ID NO 75
<211> LENGTH: 8
<212> TYPE: PRT
<213> ORGANISM: Artificial
<220> FEATURE:
<223> OTHER INFORMATION: Peptide end of cleaved Bcl10 for immunizing
      rabbit

<400> SEQUENCE: 75

Met Phe Leu Pro Leu Arg Ser Arg
1               5

<210> SEQ ID NO 76
<211> LENGTH: 12
<212> TYPE: PRT
<213> ORGANISM: Homo sapiens

<400> SEQUENCE: 76

Phe Leu Pro Leu Arg Ser Arg Thr Val Ser Arg Gln
1               5                   10

<210> SEQ ID NO 77
<211> LENGTH: 12
<212> TYPE: PRT
<213> ORGANISM: Mus musculus

<400> SEQUENCE: 77

Phe Leu Pro Leu Arg Ser Arg Ala Leu Ser Arg Gln
1               5                   10

<210> SEQ ID NO 78
<211> LENGTH: 15
<212> TYPE: PRT
<213> ORGANISM: Arabidopsis thaliana

<400> SEQUENCE: 78
```

```
Ala Gly Val Ile Lys Leu Arg Gly Leu Leu Met Glu Glu Asp Glu
1               5                   10                  15

<210> SEQ ID NO 79
<211> LENGTH: 15
<212> TYPE: PRT
<213> ORGANISM: Arabidopsis thaliana

<400> SEQUENCE: 79

Asn Lys Thr Ile Thr Ser Arg Ala Leu Pro Phe Lys Ala Val Leu
1               5                   10                  15

<210> SEQ ID NO 80
<211> LENGTH: 15
<212> TYPE: PRT
<213> ORGANISM: Picea abies

<400> SEQUENCE: 80

His Gly Ala Phe Glu Ser Arg Gly Ile His Leu Pro Ser Arg His
1               5                   10                  15

<210> SEQ ID NO 81
<211> LENGTH: 15
<212> TYPE: PRT
<213> ORGANISM: Picea abies

<400> SEQUENCE: 81

Lys Val Lys Lys Phe Val Lys Val Leu Val Thr Lys Leu Gln Ser
1               5                   10                  15

<210> SEQ ID NO 82
<211> LENGTH: 13
<212> TYPE: PRT
<213> ORGANISM: Homo sapiens

<400> SEQUENCE: 82

Met Phe Leu Pro Leu Arg Ser Arg Thr Val Ser Arg Gln
1               5                   10
```

MALT1 SPECIFIC CLEAVAGE IN ASSAY AND SCREENING METHOD

FIELD OF THE INVENTION

The present invention relates to assays and screening methods, a method for detecting Malt1-specific cleavage, isolated polypeptides, antibodies and inhibitors. The present invention also relates to the use of Malt1 as a proteolytic enzyme and the use of compounds comprising a peptide comprising an amino acid sequence according to any one of SEQ ID NO: 1-47 as substrates susceptible for specific proteolytic cleavage.

BACKGROUND OF THE INVENTION AND PROBLEMS TO BE SOLVED

Triggering of the antigen receptor of B or T cells leads to the initiation of multiple signalling pathways that regulate cellular proliferation and survival of immature and naive lymphocytes, and the effector functions of mature B and T cells. The signalling pathway that leads from antigen-receptor triggering to the activation of transcription factors of the nuclear factor-κB (NF-κB) family has a crucial role in these processes, and is controlled by highly similar molecular events in B and T cells. Genetic deficiencies in NF-κB-family members or signalling components that act upstream of NF-κB have been linked to immune deficiencies, whereas aberrant constitutive NF-κB activation has been associated with the development of autoimmune and neoplastic disorders. The understanding of the molecular mechanisms that control NF-κB activation in lymphocytes is therefore the focus of intense investigation. Recent studies have identified Carma1 (caspase recruitment domain, CARD, membrane-associated guanylate kinase, MAGUK, protein 1), Bcl-10 (B-cell lymphoma 10) and Malt1 (mucosa-associated lymphoid tissue lymphoma translocation protein 1) as signalling compounds that have crucial and specific roles in T-cell receptor (TCR)- and B-cell receptor (BCR)-induced NF-κB activation.

Malt1-deficient lymphocytes show impaired antigen receptor-induced activation of the transcription factor nuclear factor kappa B (NF-κB) and, as a consequence, impaired cytokine production and proliferation. Moreover, chromosomal translocation and abnormal expression or activity of Malt1 has been associated with formation of B-cell lymphomas of the mucosa-associated tissue.

More recently, the role of Bcl-10 and Malt1 has been extended to a role in lymphocyte adhesion, to activating signalling functions in other leukocytes such as phagocytes, mast cells and natural killer cells and to a signalling function downstream of G-protein coupled receptors, such as the receptors for lysophosphatidic acid or angiotensin II in non immune cells. This suggests that these proteins may have relevant immunomodulatory functions, but also be relevant for example in inflammation, tumour promotion and blood pressure regulation.

Dhaval N. Ghosalia at al., "Functional phenotyping of human plasma using a 361-fluorogenic substrate biosensing microarray", Biotechnology and Bioengineering, 94, 6, p. 1099-10 (2006) report enzymatic activity of 10 different plasma proteases on as many as 361 different fluorogenic substrates. The goal behind this study is to provide a microarray that gives quick information on enzymatic activity of plasma for diagnostic purposes, for example. In Table 1 a peptide substrate Ac-ARSR-ACC (ARSR: SEQ ID NO: 9) is disclosed. This reference does not concern enzymatic activity of hMalt1, the latter occurring inside cells in nature.

WO2002/33058 reports the nucleotide sequences encoding hMalt1, which is indicated as BAA83099. This reference mentions cysteine proteases, including hMalt1, and a ligand binding to the cysteine protease and inhibiting its protease activity. However, this reference does not disclose the nature of the protease activity of hMalt1 and, therefore, does not disclose a real inhibitor either.

In needs to be noted that Malt1 is known to comprise a putative active-site cysteine residue in the caspase-like domain of Malt1, as established by sequence alignments with other caspases. However, attempts to demonstrate caspase-like proteolytic activity led to the conclusion that Malt1 does not have aspartate-specific proteolytic activity (Snipas, S. J. et al., "Characteristics of the caspase-like catalytic domain of human paracaspase", Biol. Chem. 385, 1093-1098 (2004)).

In other words, while an enzymatic activity for Malt1 was hypothesised on the basis of sequence analysis, extensive experimental efforts failed to demonstrate such a cleaving activity, which is why presently the role of hMalt1 in signalling pathways is obscure.

In view of the above, it is an objective of the present invention to elucidate the role of Carma1, Bcl-10, and/or Malt1 signalling pathways, for example in B or T cells.

It is a further objective to determine the mechanism by way of which these cell components function in the signalling pathways.

It is a still further objective to provide a possibility of interfering in this pathway so as to be able to remedy the consequences and symptoms of abnormal expression or activity of Malt1, and/or other components of this or other signalling pathways.

It is, more particularly, an objective of the present invention to provide means, such as enzyme assays or screening methods, that permit the testing or screening for bioactive principles putatively interfering in a signalling pathway of cells, such as leukocytes, and in particular lymphocytes such as B and T cells.

It is also an objective to provide research tools for assisting the search and development of bioactive principles that remedy disorders and/or diseases, such as immune deficiencies, autoimmune or neoplastic disorders. Preferably, such principles are capable of affecting the cellular proliferation and survival of lymphocytes.

It is also an objective of the present invention to provide new peptide sequences, preferably useful in research and/or medicine.

Background knowledge on the field of the present invention is found in the review publications of Thome "Carma1, Bcl-10 and Malt1 in Lymphocyte Development and Activation", Nat. Rev. Immunol., 4, 348-359 (2004); and Rawlings et al., "The CARMA1 signalosome links the signalling machinery of adaptive and innate immunity in lymphocytes", Nat. Rev. Immunol., 6, 799-812 (2006).

SUMMARY OF THE INVENTION

Remarkably, the present inventors report a proteolytic activity for human Malt1. Interestingly, this activity is induced by T cell receptor (TCR) stimulation. It is also remarkable that the cleaving sequence recognized by Malt1 represents a new peptide cleaving sequence. There is currently no protease known having the same cleaving sequence specificity. These findings are useful in new enzyme assays and screening methods. They are also useful for in silico screening of potential Malt1-substrates.

Accordingly, the present invention provides, in a first embodiment, a method for detecting the occurrence of Malt1- specific cleavage, the method comprising the steps of assessing the consumption of a substrate cleaved by Malt1 enzymatic cleaving activity and/or the presence of a product obtained by Malt1 enzymatic cleaving activity. The invention also provides an assay for conducting this method.

The present invention further provides, in a second embodiment, an enzyme assay suitable to assess the consumption of a substrate and/or the production of a product, said assay comprising a substrate comprising a peptide comprising an amino acid sequence selected from any one of SEQ ID NO: 1-47, preferably 4-47, wherein said substrate is intended to be enzymatically cleaved after the C-terminal Arginine of said amino acid sequence.

In a third embodiment, the present invention provides a screening assay comprising a proteolytic enzyme and a substrate, said substrate comprising a peptide comprising an amino acid sequence selected from any one of SEQ ID NO: 1-47, preferably 4-47, said substrate being susceptible of being cleaved by said enzyme.

In a fourth embodiment, the present invention provides a method of assessing cleaving activity on a substrate having a bond to be cleaved following an amino acid sequence according to SEQ ID NO: 1-47, preferably 4-47, said method comprising the steps of contacting the substrate with a sample for which cleaving activity is to be assessed.

In a third embodiment, the present invention provides a screening assay comprising a proteolytic enzyme and a substrate, said substrate comprising a peptide comprising an amino acid sequence selected from any one of SEQ ID NO: 1-47, preferably 4-47, said substrate being susceptible of being cleaved by said enzyme.

In a fourth embodiment, the present invention provides a method of screening for a bioactive principle, the method comprising the steps of
  providing a system comprising an enzyme selected from:
    human Malt1 (SEQ ID NO:48), a non-human homologue thereof or a functional variant of any of the foregoing;
  exposing and/or contacting the system to a principle to be screened,
  measuring a proteolytic activity of the enzyme; and, optionally,
  selecting a particular principle on the basis on an effect the principle exerts on the proteolytic activity.

In a fifth embodiment, the present invention provides a compound capable of inhibiting the proteolytic cleavage catalysed by Malt1. The invention also provides a compound that is capable of inhibiting the proteolytic cleavage of human Bcl10 or a homologue thereof at a position corresponding to Arg228 of SEQ ID NO: 50.

In an embodiment, the present invention provides a compound comprising a peptide sequence according to any one of SEQ ID NO. 1-47, preferably 4-47, linked at the C-terminal end of the respective sequence to a group selected from chloromethylketone (cmk), fluoromethylketone (fmk), aldehyde (—CHO), and, said compound being optionally further substituted at the N-terminal end of said peptide.

In a sixth embodiment, the present invention provides a compound capable of inhibiting the proteolytic cleavage of a substrate peptide comprising an amino acid sequence selected from any one of SEQ ID NO: 1-47, for example 4-47, said inhibited proteolytic cleavage being at the carboxyl end of the carboxy terminal Arginine amino acid residue of said amino acid sequence. Similarly, the present invention provides a compound capable of inhibiting an enzyme selected from human Malt1 (SEQ ID NO: 48), an animal homologue of human Malt1 or a functional variant of any of the two aforementioned.

In a seventh embodiment, the present invention provides an isolated polypeptide selected from:
  (a) a polypeptide having an amino acid sequence SEQ ID. NO 50 (Bcl10 large cleaved fragment);
  (b) a homologue of SEQ ID. NO 50, or,
  (c) a variant of SEQ ID NO: SEQ ID. NO 50.

Preferably, the polypeptide of (a), (b) and/or (c) has a C-terminal -S-R amino acid sequence at the end. More preferably, the C-terminal ending of the polypeptide corresponds to the amino acid sequence according to any one selected from SEQ ID NO: 1-47, preferably 4-47. More particularly, the C-terminal sequence is selected from the groups of preferred Malt1 target sequences mentioned herein. The present invention also provides the use of such polypeptides for detecting the occurrence of enzymatic activity of Malt1.

In a further embodiment, the present invention provides a peptide having an amino acid sequence according to SEQ ID NO: 49.

In still a further embodiment, the present invention provides an isolated polypeptide selected from (a) a polypeptide having amino acid sequence SEQ ID. NO 48 including isoforms; (b) a functional homologue of SEQ ID. NO 48; and, a variant of any of the polypeptides defined under (a) or (b), wherein said polypeptide has proteolytic activity, in particular human Malt1-specific proteolytic activity.

In further embodiments, the present invention provides the use of human Malt1, functional homologues or variants thereof as a specific protease, and a method of cleaving a substrate, the method comprising the step of contacting the substrate with human Malt1, a functional homologue and/or a variant thereof. The present invention also encompasses the use of human Malt1 in enzyme assays.

In still further embodiments, the present invention provides the use of substances comprising an amino acid sequence selected from any one of SEQ ID NO: 1-47, for example 4-47 as cleavable substrates, for example in enzyme assays and/or screening methods.

In yet another embodiment the present invention provides an antibody specifically binding to a product of Malt-1 specific cleavage. For example, the antibody binds to Bcl10, a homologue or variant thereof as cleaved by Malt1. Preferably, the antibody does not bind to Bcl10 not cleaved by Malt1, the antibody thus specifically detecting only the cleaved specimen.

In another embodiment, the present invention provides a method of preparing and/or designing an inhibitor of Malt1 proteolytic cleaving activity, the method comprising the steps of: (a) providing a peptide comprising an amino acid sequence according to any one of SEQ ID NO: 1-47, preferably 4-47 or any of the preferred sequences selected from SEQ ID NO: 1-47 as defined in the present specification; (b) modifying said peptide, preferably by using peptidomimetics approaches, thereby obtaining a modified peptide; (c) exposing said modified peptide to enzymatically active Malt1, a homologue and or functional variant thereof; (d) determining the presence or absence of inhibition of Malt1 proteolytic cleaving activity; and, if no inhibition is found, (e) repeating the previous steps, whereby in step (b) modification of the peptide is such that a modified peptide is obtained that is structurally different from any modified peptide obtained previously.

In yet another embodiment the present invention provides a method for in silico screening for putative substrates of Malt1, a homologue or variant thereof, the method comprising the steps of systematically looking for any of SEQ ID NO: 1-47, for example 4-47 or for the nucleotide sequences encoding any of SEQ ID NO: 1-47, for example 4-47 in a database comprising amino acid or nucleotide sequences of an organism, for example the genome of an organism. For example, the open reading frames of the genome of the organism may be screened.

Further aspects and embodiments of the present invention are provided in the appended claims.

BRIEF DESCRIPTION OF THE DRAWINGS

In FIG. 2a, cells were pre-incubated with different protein kinase inhibitors before lysis. In FIGS. 2b-e, cells transfected or transduced as indicated or with the expression of specific cellular proteins silenced by shRNA are compared.

FIG. 3 b shows an alignment of the C-terminal amino acid sequence of human and murine Bcl10 with previously identified metacaspase cleavage sites identified in Serpin1 and metacaspase9 of A. thaliana (AtSerpin1 and Atmc9) and in metacaspase type II of P. abies (mcIIa-Pa).

FIGS. 3 c and d show western blots of lysates of transduced and transfected cells. In FIG. 3c, Jurkat T cells expressing either a wild-type form of Bcl10 or a point mutated, non-cleavable form of Bcl10 are compared following stimulation of the cells with the cell stimulants PMA (phorbol myristate acetate) and ionomycin. In FIG. 3d, 293T cells expressing various FLAG- or VSV-tagged Malt1-mutated or Bcl10-mutated cells are compared.

In FIG. 6a, cleavage activity after various stimulation times are shown, whereas in FIG. 6b incubation with T-cell stimulants was for 20 minutes and cleavage of LRSR-amc over time is compared for T cells transduced with control or Malt1-specific shRNA.

FIG. 9 shows the presence of cleaved Bcl10 in lymphoma samples. Bcl10 cleavage was assessed in Western blot using lymphoma tissue lysates from patients with mucosa-associated lymphoid tissue (MALT) lymphoma, diffuse large B-cell lymphoma (DLBCL), follicular cell lymphoma (FCL) or mantle cell lymphoma (MCL). Controls include lysates of non-stimulated (−) and PMA/ionomycin-stimulated (+) $CD8^+$ T cell clones.

FIG. 10 a and b show sequence alignments of amino acid sequences originating from different species and also from a virus. The sequences are aligned on a target cleaving sequence that can be cleaved by hMalt1. FIG. 10A shows experimentally established cleaving sites of natural substrates in stimulated lymphocytes. FIG. 10B shows cleaving sites identified upon artificial co-expression of hMalt1, the substrate comprising the indicated sequence, and hBcl10 in 293T cells. In the case of Malt1 auto-cleavage (SEQ ID NO: 61 in FIG. 10B), the wild type hMalt1 is co-expressed with hBcl10. In this experiment, respective R-mutants of the proteins listed in FIG. 10B are no longer cleaved. Data obtained with SEQ ID NO: 59 (vE10) is not definite.

FIGS. 11 a-f illustrate the inhibition of hMalt1 cleaving activity by Malt1 inhibitors of the present invention. In FIG. 11a recombinant purified GST-Malt1 protein, oligomerized by binding to glutathione sepharose, was tested for LRSR-amc clavage activity in the absence (black bars) or presence (bright bars) of increasing concentrations of the inhibitor z-VRPR-fmk (VRPR: SEQ ID NO: 65) described herein, resulting in reduction of cleavage activity in dependence of the concentration. Figs. b and c show western blots of lysates of Jurkat and CTL cells, respectively, showing Bcl10 of cells activated by PMA and ionomycin for the indicated times and exposed or not to the inhibitor z-VRPR-fmk (VRPR: SEQ ID NO: 65). Figs. d and e show the effect of the same inhibitor on the NF-kB and IL-2 response in Jurkat T cells activated as indicated, and Fig. f shows the effect of the presence of the inhibitor on adhesion to fibronectin of Jurkat T-cells following activation or not, as indicated.

Figure 1:
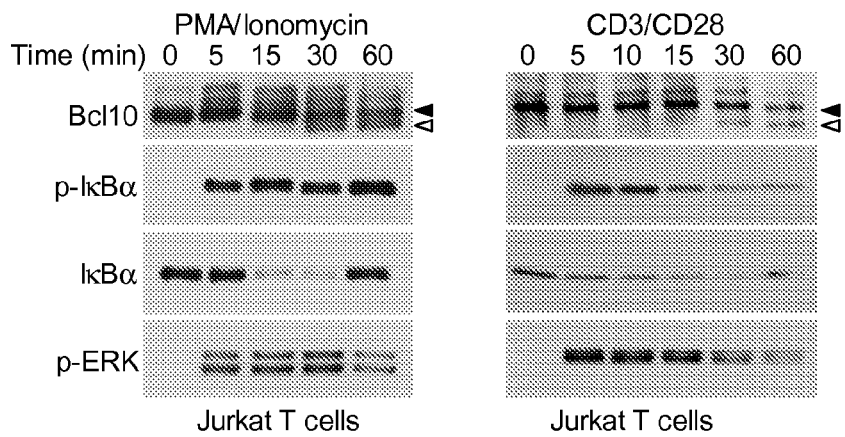
FIGS. 1 a-c show western blots of lysates of a T cell-line (Jurkat), human cytotoxic T cell clones and a B-cell line (Raji) as indicated following stimulation of the cells with various TCR stimulants or reagents mimicking T- or B-cell activation. The stained proteins are involved in signalling and are used here to assess efficient lymphocyte activation. In all Figures, black arrowheads indicate the position of unmodified Bcl10, while white arrowheads indicate a faster migrating fond). of Bcl10.
Figure 1:
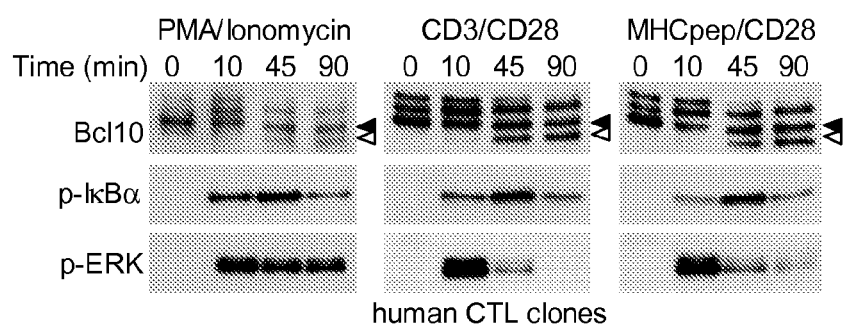
Figure 1:
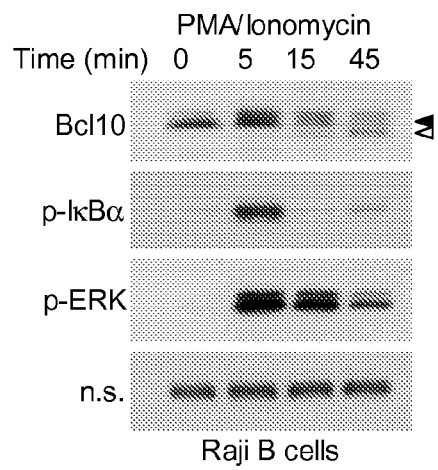

The attached sequence listing is integral part of the present specification. SEQ. ID. NOs: 1-47 show target sequences that are specifically recognized and cleaved at the C-terminal Arginine residue by Malt1. SEQ ID NO: 48 is the amino acid sequence encoding hMalt1, which was described previously.

SEQ ID NO: 49 is the shorter of two proteolytic cleavage products of Malt1 on hBc110, while SEQ ID NO: 50 shows the larger of the two peptide products. SEQ ID NO: 51 is the amino acid sequence encoding hCARMA1 as previously described. SEQ ID NOs: 52-61 are extracts of sequences of various organisms, aligned for comparison and for the determination of a consensus sequence in FIGS. 10A and B. SEQ. ID. NOs: 62-64 are sequence extracts of polypeptides, which sequence extracts can also be aligned with SEQ ID NOs: 52-61.

DETAILED DESCRIPTION OF THE PREFERRED EMBODIMENTS

The embodiments of the present invention are based on the finding of a proteolytic activity of human Malt1 (hMalt1) and on the finding of so far unknown peptide target cleavage sequences for which hMalt1 is specific. The present inventors further found that the proteolytic activity of hMalt1 plays an important role in the adaptive immune response through its contribution in signalling pathways of the B-cell and T-cell receptors. The proteolytic activity of Malt1 described herein is equally important for other receptors that signal via Malt1. For example, these include receptors that signal via ITAM (immunoreceptor tyrosine-based activation motifs), such as for example receptors of the FcR family and pathogen receptors similar to Dectin-1, and G-protein coupled receptors such as for example the receptors for lysophosphatidic acid or for angiotensin II, which has pro-inflammatory effects and effects on blood pressure. The involvement of Malt1 in these pathways is reviewed in an article by Wegener and Krappmann: "CARD-Bcl10-Malt1 signalosomes: Missing link to NF-kB", SciSTKE2007, pe21 (2007).

For the purpose of the present invention, the expression "Malt1-specific cleavage" refers to cleavage resulting from enzymatic cleaving activity of the enzyme hMalt1, a homologous protein of hMalt1 of another species and from a functional variant of any of the foregoing. The expression "hMalt1" encompasses different isoforms of the protein according to SEQ ID NO: 48 found in humans.

In vivo, "Malt1-specific cleavage" refers to intracellular enzymatic cleavage activity. Of course, enzyme assays using isolated and/or recombinant hMalt1, a functional homologue or variant thereof may be provided, so that the hMalt1 specific cleavage is conducted in a system, which is free of cells and/or in the extracellular matrix.

"Malt1-specific cleavage" is preferably characterised by the specificity of suitable peptide target sites where cleavage can occur. Accordingly, "Malt1-specific cleavage" refers to the cleavage of molecules comprising the specific target cleaving sites mentioned herein. In particular, it refers to cleavage of molecules comprising any one of SEQ ID NO: 1-47, in particular 4-47, and/or molecules comprising any one of SEQ ID NO 52-61 (Sequence alignment of FIG. 11), preferably, comprising any one of preferred peptide target sequences of suitable substrates mentioned herein.

Accordingly, the present invention provides a method, an assay and a screening method in which the Malt1-specific proteolytic activity is assessed.

The term "assess" or "assessment" used with respect to the enzyme or screening assay of the invention and also with respect to the methods of the invention, refers to one or more activities related to the qualitative finding of presence or absence of an enzymatic activity as specified, the quantitative approximation of such activity, for example in terms of rate of product consumption, relative comparison of activities, and/or also the quantitative measurement of such activity, for example.

Proteolytic activity or proteolytic cleavage, in the context of the present invention, preferably refers to the cleavage of a covalent bond of one or more compounds of formula (I) to (IV) below,

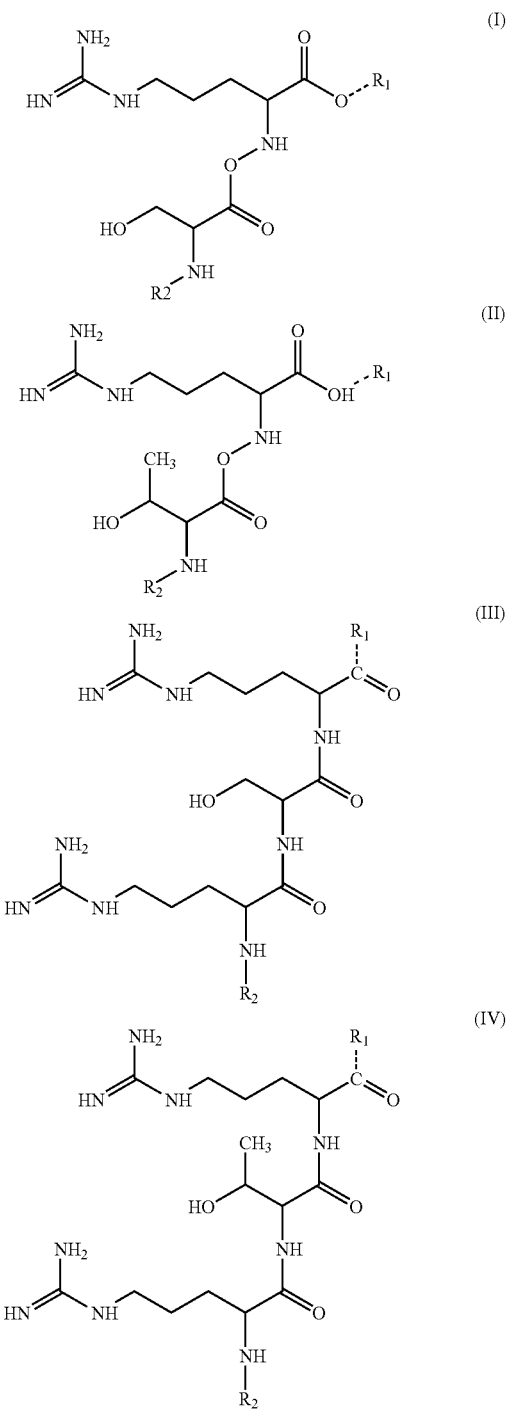

wherein the covalent bond being cleaved is indicated as a dashed line and wherein $R_1$ and $R_2$ refer to organic residues including organometallic compounds and complexes, and wherein $R_2$ can also be H. Preferably, the compounds of formula (I)-(IV) comprise an amino acid sequence selected from any one of SEQ ID NO: 1-47, in particular 4-47, and/or any one of the amino acid sequences which are underlined in FIGS. 10A and 10B (from SEQ ID NOs 1, 2 and/or from SEQ ID NO: 52-61).

For example, $R_2$ is -Leu-$R_3$, with $R_3$ being an organic residue including organometallic compounds or —H. Preferably, $R_1$ is —NH—$R_3$. An organic residue is a hydrocarbon optionally substituted and optionally comprising one or more heteroatoms. For example, $R_1$ and $R_2$ comprise and/or consist of peptides such as mono-, di-, tripeptides, oligopeptides (3-10 amino acids) and/or polypeptides (>10 amino acids). Preferably, these peptides are peptides comprising and/or consisting of L-amino acids, more preferably amino acids selected from the 20 standard proteinogenic amino acids. $R_1$ and $R_2$ may be the same or different. $R_1$ and/or $R_2$ may be proteins having a specific enzymatic activity. Furthermore, $R_1$ and $R_2$ may be compounds having any specific biologic activity or fluorescence or phosphorescence, for example.

The covalent bond to be cleaved preferably is a C—N bond, for example a peptide bond. It may also be a C—C bond, or a C—O bond, for example an ester or ether bond.

In compounds (I)-(IV), the amino acid moieties Arg, Ser and/or Thr may be chemically modified, for example in order to improve cell permeability of the substrate. For example, any one or both of the free amino group of the Arg-residues may be C1-C4-alkylated, preferably methylated.

Herein below, compounds (I)-(IV), the principle substrates of the enzyme assay and screening method of the present invention, will also be referred to as $R_1$—R—S—R—$R_2$ and $R_1$—R-T-R—$R_2$, with R, S and T standing for Arginine, Serine, and Threonine. For the purpose of the present specification, if peptide sequences are indicated with amino acids abbreviated by the one- or three letter code from left to right, the N-terminal end of the sequence is indicated left and the C-terminal end of the sequence is indicated right, as is conventional.

Accordingly, the term "substrate" for the present invention encompasses dipeptides, tripeptides, oligopeptides and polypeptides as well as derivatives thereof. In this sense, the term substrate includes compounds comprising a peptide comprising an amino acid sequence as defined in any one selected from SEQ ID NO: 1-47, in particular 4-47. Preferably, the substrate comprises and/or consists of a tri- or an oligopeptide having 3 to 10 amino acids.

The sequences of SEQ ID NO: 1-47, preferably 4-47, are also referred herein as the target cleaving sequence.

According to a preferred embodiment, the substrate comprises a peptide comprising an amino acid sequence of Xaa-R- (SEQ ID NO: 1), wherein Xaa stands for the any one amino acid selected from the groups of S, T, V, and G. Preferably, the substrate comprises a peptide comprising an amino acid sequence of -S/T-R- (selected from the group of SEQ ID NO: 2 and 3). More preferably, the substrate comprises a peptide comprising an amino acid sequence of -S-R- (SEQ ID NO: 2), wherein said substrates are cleaved by Malt1 following the carboxyl terminus of the R (Arg) residue. For example, according to an embodiment, the substrate comprises a peptide comprising an amino acid sequence of -R-S/T-R- (selected from the group of SEQ ID NOs.: 4 and 5). For example, said amino acid sequences of said substrates are provided in a larger peptide comprising further amino acids or amino acid sequences at the C-terminal of the indicated target sequence.

Preferably, the substrate comprises a peptide that comprises an amino acid sequence selected from any one of SEQ ID NO: 4, 5, 8-47, in particular any one of 5, 4, 11, 13, 23, 31, 33 and/or 43.

Preferably, the substrate comprises an amino acid sequence as defined by the general consensus sequences according to SEQ ID NO: 6 and/or 7, with Xaa standing for any amino acid but preferably L, P or H. According to a preferred embodiment, the substrate comprises an amino acid sequence selected from LRSR and LRTR (SEQ ID NOs: 11 and 31).

According to an embodiment, the substrate comprises an amino acid sequence of at least 5 amino acids, said five amino acids being an N-terminal Proline followed by an amino acid sequence comprising 4 amino acids according to any one of SEQ. ID. NO 8-47 (P-G-R-S-R (SEQ ID NO: 66), P-A-R-S-R, (SEQ ID NO: 67) etc.), preferably, PLRSR, PHRSR, PPRSR, PLRTR, PHRTR, and/or PPRTR (SEQ ID NOs: 68-73).

The substrate comprising an amino acid sequence according to any one of SEQ ID NO: 1-47, preferably 4-47, may be provided in the form of a modified peptide. Modifications contemplated by the invention include, but are not limited to, pegylation (PEG linkage), glycosylation, amidation, carboxylation, phosphorylation, or addition of an acetyl, myristic, palmitic, stearic, or acidic group, creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus. These modifications may also occur at amino acids that form part of the target cleaving sequence according to any one of SEQ ID NO: 1-47, preferably 4-47.

Accordingly, substrates according to the invention are Bcl10 of *Homo sapiens* (NCBI accession number CAH71557), *Mus musculus* (NP 033870), *Rattus norvegicus* (NP 112618) or *Bos Taurus* (AAI18327), these proteins all being characterised by the target cleaving sequence LRSR (SEQ ID NO: 11). Another substrate is vE10 of Equine herpesvirus 2, which contains a LRTR (SEQ ID NO: 31) target sequence. Furthermore, Carma1 of *Homo sapiens* (NP 115791), *Mus musculus* (NP 780571), *Bos taurus* (XP 593388) or *Canis familiaris* (XP 547005) are also potential substrates.

According to an embodiment, the substrate is (a) human Bcl10 (hBcl10), (b) a non-human homologue thereof, or (c) a variant of any of (a) or (b). HBcl10 corresponds to the peptide according to SEQ ID NO: 50 with the short peptide SEQ ID NO: 49 being added at the C-terminal end of SEQ ID NO: 50.

A homologue of a specific peptide of reference (the "original" peptide) mentioned herein is another peptide occurring in another species than the original peptide *Homo sapiens* but sharing the ancestry with the original peptide. Preferably, a homologue according to the present invention may or may not perform the same function in its natural environment as the original peptide reported herein. Rodent homologues of human Bcl10, for example, are indicated above.

A variant peptide is a peptide differing from an original peptide in that the original peptide has been chemically modified. For example, amino acid residues of the original peptide have been deleted, added or changed, but which still is capable of fulfilling substantially the same function as the original peptide. Variant polypeptides encompass peptides in which specific amino acid residues have been replaced by similar amino acids, such as amino acids having similar properties. For example, a variant peptide would be a peptide in which an amino acid having a hydrophobic residue has been replaced by an amino acid having another hydrophobic residue, or in which an acidic amino acid by another, similarly acidic amino acid, and so on. Variant peptides also include compounds resulting from chemical modification of an original peptide, in particular original peptides comprising markers suitable to detect and/or quantify the peptide or a fragment thereof. A variant also encompasses a peptide obtained by gene shuffling using a nucleotide sequence encoding the original peptide. Gene shuffling is often used to improve the desired activity of an enzyme by creating mutated genes encoding a variant of the original enzyme and selecting those variants having improved characteristics.

Preferably, in a variant peptide, the domain or amino acid sequence corresponding to that of the original peptide (excluding added sequences e.g. with fusion peptide variants) has at least 40%, 50%, 60%, 70%, 80%, 85%, 90%, 95% or 97% amino acid sequence identity with the original peptide as referred to herein.

The reference to a protein and/or peptide, for the purpose of the present invention, also includes a reference to naturally occurring isotypes. Preferably, these isotypes are able to fulfil the same function as required for the purpose of the present invention, or the isotype is provided in a variant form capable of fulfilling the function.

According to a preferred embodiment, the substrate comprises a marker molecule, for example marker peptides, suitable for assessing, preferably quantifying, the consumption of the substrate and/or the production of the product.

For example, suitable marking systems could be substrates in which cleavage induces the loss of fluorescence activated energy transfer (FRET) between suitable donor/acceptor pairs that would be added on suitable sites within the substrate which are preceding and following the cleavage site (for example the N- and C-terminus of a substrate peptide). This would allow to assess a loss of FRET upon cleavage because of the resulting separation of acceptor and donor moieties. A similar principle could be used to change (for example, destroy or obtain) any physical, chemical, or biological (e.g. enzymatical) property depending on proximity of two sub-units/protein parts for functionality. For example, it is possible for a marker of hMalt1-specific proteolytic activity to obtain measurable physical, chemical or biological property, such as fluorescence, enzymatical or other biological activity through cleavage of the substrate.

It would also be possible to immobilise the substrate via one particular part of it (for example the free amino terminus of the peptide) and to assess proteolytic release of a measurable enzymatic or radioactive or fluorescent activity that has been covalently or not covalently linked to the substrate (for example to its C-terminus as part of $R_1$) and that would be released into the supernatant upon incubation with samples containing proteolytically active Malt1.

For example, the substrate comprises a fluorescent compound, for example 7-amino-4-methylcoumarin (AMC) or a fluorescent derivative thereof, linked to the C-terminal Arginine of the target cleaving sequence, and wherein substrate consumption or product production is assessed by measuring, approximating and/or comparing fluorescence intensity of cleaved AMC or the fluorescent derivative thereof.

An antibody specifically binding to a product of Malt1-specific cleavage is encompassed by the invention and may also be used as a marker for detecting Malt-1 cleaving activity, in particular to a product obtained from Malt1 specific cleavage. Preferably, the antibody does not bind to a substrate from which said product is obtained by Malt1-specific cleavage. Preferably, the antibody of the invention specifically binds to cleaved Bcl10, such as the polypeptide of SEQ ID NO: 49, but does not bind to a Bcl10 not having the C-terminal amino acid sequence of SEQ ID NO:49. This C-terminal amino acid sequence preferably involves a sequence of the at least 4, more preferably the at least 6 and most preferably the at least 8 amino acids of the C-terminus of SEQ ID NO: 49.

In the assay and the method of screening of the present invention, a substrate consumption and/or product production is preferably catalysed by human Malt1, a homologue thereof and/or a variant thereof. For example, a variant hMalt1 comprising and/or consisting essentially of the caspase-like domain of hMalt1 or of a homologue thereof may be suitable. The caspase-like domain of hMalt1 is the sequence stretching from aa 336-572 of SEQ ID NO: 48. Depending on the scientist and sequence analysis program used, the caspase-like domain of hMalt1 may comprise a few amino acids more or less on either side. These caspase-like domains provide the cleaving activity of hMalt1, homologues and/or functional variants thereof. Variants comprising all or part of the caspase-like domain are therefore examples of functional variants of hMalt1. Of course, in variants comprising all or part of aa 336-572 of SEQ ID NO: 48, individual amino acids may be exchanged and/or omitted, while the cleaving activity is retained. For example, amino acids may be classified as polar and apolar, as acidic, neutral and (weakly) basic. It is common to provide peptide variants in which amino acids having similar properties while retaining the activity. Such variants are also included herein.

Other enzymes, so far not described, may have the same cleaving activity as defined above and may be used instead. With the teaching of the present invention it is now possible to more specifically search and identify other enzymes having the same activity.

Accordingly, the enzymatic activity reported herein may be accomplished by hMalt1 according to SEQ ID NO: 48. Various isoforms of hMalt1 have been reported so far, for example under accession number BAA83099 in the NCBI protein database. Isoforms of proteins mentioned herein are also encompassed by the present invention.

The assay of the present invention may be provided in the form of a kit comprising various components, one of which being, for example, a substrate as defined above susceptible of hMalt1-specific cleavage. The term assay as used in this description also encompasses a kit.

The enzyme having hMalt1-specific cleaving properties may be a component of the assay, the assay being provided in the form of a kit comprising various components. Preferably, however, the enzyme may be included in a sample to be tested and is, in this case, provided by the user of the assay.

The assay may be used to assess the activity of an enzyme by exposing cells to a substrate as defined herein. Cells may be any cells of interest, including human and/or non-human cells. In particular, the cells may be human, animal, plant and/or bacterial cells. The cells may be provided in the form of a sample of human or animal, for example, rodent, tissue. The sample to be tested may be provided in the form of a slice of tissue of a human or an animal. The sample may contain blood cells, in particular lymphocytes, for example B- or T-lymphocytes. In particular, the sample may be a tumor tissue sample, for example a lymphoma sample.

Cells to be tested may or may not be pre-treated ("activated") before testing enzymatic hMalt1-specific cleaving activity. For example, cells may be exposed to specific substances for testing the effect of these compounds on the hMalt1-specific cleaving. Such substances may be substances activating TCR- or BCR-mediated cell signalling cascades, such as those mentioned in the examples below. Such substances may be part of the assay or may be separately obtained and applied by a user of the assay. Such activating substances may form part of the assay.

Preferably, cells are preferably destroyed, for example lysed, to provide a sample for which the occurrence of Malt1-specific cleavage can be detected. Since Malt1-specific cleavage occurs in the intracellular space, destruction of cells naturally expressing Malt1 is preferred in order to assess the consumption of a substrate and/or the presence of a product of Malt1-specific cleavage. Lysis facilitates the contact of the substrate with hMalt1-specific cleaving enzymes present in the cells.

Preferably, the enzymatic activity is assessed in presence of a specific buffer enabling hMalt-specific enzymatic activity. Buffers suitable for assessing hMalt1-specific enzymatic activity are preferably buffers with physiological pH and ionic strength, for example 20 mM Tris/HCl and 150 mM NaCl, and preferably comprising a reducing agent, for example dithiothreitol or mercaptoethanol. Preferably, the buffer contains $Ca^{2+}$ ions. Furthermore, buffers may contain inhibitors of proteases and/or phosphatases to avoid degradation of the substrate by other, non-specific proteases.

Suitable protease and/or phosphatase inhibitors not inhibiting hMalt1-specific cleavage and/or suitable buffers may be part of the assay.

The present invention also provides an assay, in particular a screening assay and/or a screening method. One goal of these aspects of the present invention is to provide a possibility of assessing the effect of a principle to be screened on hMalt1-specific cleaving.

In a step of the screening method, a system comprising an enzyme capable of hMalt1-specific cleaving is provided. For example, the system may comprise hMalt1, a homologue and/or derivative there from. The enzyme may, for example, be provided in the form of cells as defined above, said cells comprising the enzyme. For example, cells transfected or transduced to express increased amounts of hMalt1 may be used. Instead of using cells, it is preferable to use purified and/or isolated enzyme, for example enzyme produced in a suitable expression system. Preferably, the enzyme is recombinant.

The system comprising the enzyme preferably comprises co-factors assisting the proteolytic cleavage. In particular, the system preferably comprises a peptide selected from human Carma1 (SEQ ID NO: 51), a non-human homologue thereof and/or a functional variant thereof. It was shown in the present invention that Carma1, in particular its binding to Bcl10 and its oligomerization, may play a role in optimal hMalt1-specific cleavage. As with the enzyme providing hMalt1-specific cleaving, Carma1 may be provided in the form of cells expressing Carma1, or in a recombinant, preferably purified form.

The system also preferably comprises a peptide selected from Bcl10, a non-human homologue thereof and/or a functional variant thereof, since the capacity of Carma1 to bind Bcl10 (which mediates formation of a Carma1-Bcl10-Malt1 complex) seems to be required for activation-induced Bcl10 cleavage by Malt1.

Of course, isolated Carma1, hMalt1 and further selected components may be provided together in a purified preparation. These components may be provided in any method and/or assay of the present invention. For example, Carma1 and/or Bcl10 may be provided in a purified preparation, or even all three together.

Preferably, if recombinant Malt1 is used for the purpose of the present invention, for example in the screening method, a recombinant Malt1 form is selected that contain oligomerization domains or that contain protein domains that can be inducibly oligomerized by addition of suitable bi-valent or multivalent compounds. The recombinant Malt1 may also be chemically modified to allow inducible oligomerization. The necessity of oligomerization is explained by the fact that a role of Carma1 seems to be the induction of an oligomerization of Malt1.

The components used for the screening method, such as the enzyme as well as the substrate and optional cofactors, buffers, and the like may be used as indicated with respect to the assay described above. For example, the system comprising the enzyme is an aqueous solution or suspension to which a purified form of the enzyme and, optionally cofactors have been added. Accordingly, the present invention also relates to a screening assay suitable for conducting the screening method. The screening assay may also be provided in the form of a kit.

Preferably, the screening method of the present invention comprises the step of comparing the measured proteolytic activity of the enzyme to a control proteolytic activity measured in absence of the principle to be screened.

Preferably, the screening method of the present invention comprises the step of comparing the measured proteolytic activity of the enzyme to a control proteolytic activity measured in presence of a control principle of which the effect (e.g. activation, inhibition or stabilisation) on the enzyme is known.

Generally, the screening method comprises the step of assessing if the principle to be screened exerts an effect on said proteolytic activity by comparing the measured proteolytic activity with the control proteolytic activity and by finding an effect if said activity and said control activity differ from each other.

The effect that the principle to be screened exerts may be selected from an inhibitory effect or an activating effect, wherein an inhibitory effect is found if said proteolytic activity is lower than said control proteolytic activity and/or wherein an activating effect is found if said proteolytic activity is higher than said control proteolytic activity.

The present invention also provides an inhibitor, in particular (1) a compound capable of inhibiting the proteolytic cleavage of a substrate polypeptide at the carboxyl end of the Arginine amino acid residue at a cleavage site having an amino acid sequence selected from any one of SEQ ID NO: 1-11, or from any one of 4, 5, and 8-11; (2) a compound capable of inhibiting the proteolytic cleavage of human Bcl10 or a homologue thereof at a position corresponding to Arg228 of SEQ ID NO: 49 (hBcl10, cleaved).

Such an inhibitor can be an antibody and/or a peptide comprising an amino acid sequence selected from any one of SEQ ID NO: 1-47, preferably 4-47.

The inhibitor may be a monoclonal or polyclonal antibody.

Preferably, the inhibitor is a compound capable to bind to the proteolytically active site of human Malt1, including compounds binding to or covering sites Cys464 and/or His415 of SEQ ID NO: 48. Alternatively, the inhibitor binds to or associates with other portions of Malt1, for example portions outside the caspase-like domain, said compound inhibiting proteolytic activity of Malt1 by said binding or association to said other portions of Malt1, for example by inducing conformational changes affecting the proteolytically active site.

The present invention particularly relates to inhibitors comprising the target peptide sequence. These are substrate-mimetic inhibitors that comprise the Malt1 recognition sequence (any one of SEQ ID NO: 1-47, in particular 4-47, such as SR and preferably RSR, RTR, in particular RPR) linked to reactive groups such as chloromethylketone (cmk)

or fluoromethylketone (fmk), for example, that irreversibly inhibit; or aldehyde (CHO) reactive groups that reversibly inhibit the active site of Malt1. To increase cell permeability, the peptides can be N-terminally modified with Ac (acetyl) or Z (benzyloxycarbonyl) groups and the amino groups of the arginine residues can be alkylated, for example with a C1-C10, preferably C1-C5 alkyl, preferably methylated, for example. Other ways of increasing cell permeability are also encompassed within the scope of the present invention. As another example, the peptides may be biotinylated, for example N-terminally. A biotinylated inhibitor is useful as a research tool to inhibit and subsequently isolate caspases, for example by pull-down assays using avidin- or streptavidin-coupled supports. According to yet another embodiment, the inhibitor comprises a fluorescent grouping. For example, fluorescent FITC (Fluorescein isothiocyanate) may be linked N-terminally to the peptide group of the inhibitor to yield FITC-RSR-fmk (RSR: SEQ ID NO: 4), or FITC-VRPR-fmk (VRPR: SEQ ID NO: 65), for example.

According to an embodiment, at least one amino group of an arginine residue of said peptide is alklyated, for example with an C1-C10, preferably a C1-C5 alkyl.

According to an embodiment, the inhibitor is the compound X-VRPR-Y (VRPR: SEQ ID NO: 65), wherein X is selected from H, Ac, Z, biotinyl, a fluorescent substituent and from other substituents providing a desired functionality to the compound, and Y is selected, independently of X, from fmk, cmk and —CHO.

In general, inhibitors of the present invention may be functionalised as desired, preferably at the N-terminal end of the peptide fragment, in order to adapt it to a specific purpose, which increases its utility as a research tool.

An inhibitor that showed inhibition of Malt1-specific cleaving is z-VRPR-fmk (VRPR: SEQ ID NO: 65). This inhibitor may be used as such, for example in research and/or in vitro testing, such as in vitro enzymatic assays of this invention. This inhibitor may also be useful for in vivo applications, for example as a medicament and in the treatment and/or prophylaxis of the conditions mentioned below. According to preferred embodiment, an inhibitor having improved in vivo characteristics, such as fewer side effects and comparatively low toxicity and overall improved pharmacological properties is designed on the basis of the indicated z-VRPR-fmk (VRPR: SEQ ID NO: 65) by peptidomimetics. Such an inhibitor may be synthesized according to the methodology disclosed in the following publications: Bioorganic & Medicinal Chemistry, Volume 5, Issue 5, May 1997, Pages 797-807. E. Ponnusamy, U. Fotadar, A. Spisni and D. Fiat, A novel method for the rapid, nonaqueous tert-butoxy-carbonylation of some O-17-labeled amino-acids and O-17-NMR parameters of the products, Synthesis (Stuttgart) 1 (1986), pp. 4849.

Accordingly, the present invention encompasses peptidomimetics of the target sequence peptides of SEQ ID NO 1-47, in particular 4-47, in particular RSR, RTR and RPR, optionally comprising further amino acids. The peptidomimetics may comprise the same chemical modifications as indicated for the peptide substrate sequences SEQ ID NO 1-47 above (pegylation, glycosylation, etc.).

The present invention also provides a method for obtaining an inhibitor capable of inhibiting Malt1-specific cleaving and/or a compound for preventing and/or treating the conditions indicated below. The method comprises the steps of designing and testing peptidomimetic compounds for their Malt1-specific cleaving inhibitory activity. Drug design according to peptidomimetics has been discussed in the art. For example, Walensky et al., Science 2004; Sep. 3; 305 (5689): 1411-3, describe hydrocarbon stapling for obtaining peptidomimetics having improved pharmacological properties. Li L. et al, Science 2004 Sep. 3. describe a small molecule mimic of Smac, a pro-apoptotic protein. Rubin-Carrez C. published on the internet a report entitled "des peptidomimetiques peptidiques aux mimetiques non peptidiques: sur la voie du medicament.", which sets out some of the methodology currently use for developing peptidomimetics.

For example, the substitution of classic peptide bonds by isosteric amides resistant to peptidases is mentioned in this report, amongst many other ways. The above references are entirely incorporated herein by reference. The present invention thus encompasses peptidomimetic compounds of the peptide-based inhibitors reported herein.

The method of screening of the present invention may be a method for screening for principles having at least one of the effects selected from: (1) immunomodulation, (2) modulation of inflammatory processes, (3) suppressing an immune reaction, (4) reducing or avoiding an immune reaction against a transplant, (5) reducing and/or increasing blood pressure, (6) reducing cellular proliferation. Medicaments with these effects may be prepared from active principles selected by the screening method of the present invention.

The screening method of the present invention is susceptible of identifying inhibitors and/or principles that are useful as a medicament. For example, the principle may be used for the prevention or treatment of (1) lymphomas and/or leukaemia, (2) an immunological disorder, (3) multiple sclerosis, (4) an autoimmune disease, (5) diabetes, (6) allergies, (7) hemic disease, in particular hemic tumours, (8) tumours in general, (9) inflammatory disorders, for example colitis, arthritis and/or artheriosclerosis, or combinations of two or more of the aforementioned.

The present invention also provides inhibitors identified by the screening method, the inhibitors potentially having the characteristics indicated above. Accordingly, inhibitors may be used as medicaments.

The present invention will now be illustrated by way of examples. These examples do not limit the scope of this invention which is defined by the appended claims.

EXAMPLES

Example 1

Analysis of Human T Cell Lines and Observation of Faster Migrating Bcl10 Species Cells Used for the Experiments Blood samples were obtained from two HLA-A*0201 positive healthy volunteers containing readily detectable frequencies of EBV- and CMV-specific CD8$^+$ T-cells in ex-vivo analyses. From these blood samples, peripheral blood mononuclear cells (PBMCs) were obtained by density centrifugation using Ficoll-Hypaque (Pharmacia, Uppsala, Sweden) and cryopreserved in RPMI 1640 supplemented with 40% FCS and 10% DMSO ($1 \times 10^7$-$2 \times 10^7$ cells per vial) until further use. Phycoerythrin-labeled HLA-A*0201/peptide multimers were prepared with NLVPMVATV (SEQ ID NO: 74) peptide (CMV/pp65$_{495-503}$) and were kindly provided by P. Guillaume and I. Luescher (Ludwig Institute for Cancer Research, Epalinges, Switzerland). Multimer-positive CD8$^+$ T-cells were sorted by a FACSVantage® SE using CellQuest software (Becton Dickinson), cloned by limiting dilution, and expanded in RPMI 1640 medium supplemented with 8% human serum (HS), 150 U/ml of recombinant human IL-2 (rIL-2; a gift from GlaxoSmithKline), 1 µg/ml phytohemagglutinin (PHA; Sodiag, Losone, Switzerland) and $1 \times 10^6$/ml irradiated allogeneic PBMC (3000 rad) as feeder cells. Positive EBV- and CMV-specific T-cell clones (cytotoxic T lymphocytes, CTL) were periodically (every 15 days) re-stimulated in 24-well plates with PHA, irradiated feeder cells, and rIL-2.

The human cell lines Jurkat (J77 clone 20), Hut78 and Raji cells (all are gifts of Oreste Acuto, Pasteur Institute, Paris) were grown at 37° C. in RPMI 1640 supplemented with 10% FCS and antibiotics.

Stimulation of Cells

For short term stimulations, cells were re-suspended at a density of $5 \times 10^7$ cells/mi in RPMI with 0.5% serum and pre-warmed for 10 min at 37° C. before addition of the stimulating agent.

T-cell stimulation was initiated by addition of PMA (10 ng/ml, Alexis) and ionomycin (1 µM, Calbiochem) (P/I) or a combination of anti-human CD3ε (10 µg/ml of OKT3, Apotech) and anti-CD28 (10 µg/ml of CD28.2, Immunotech) antibodies (CD3/CD28), immediately followed by addition of 5 µg/ml of cross-linking goat anti-mouse antibody (Southern Biotech).

Pooled human CMV-specific CTL clones were stimulated by 10 µg/ml MHC-pep tetramers (HLA-A*0201/peptide multimers with NLVPMVATV (SEQ ID NO: 74) peptide corresponding to CMV/pp65$_{495-503}$, kindly provided by P. Guillaume and I. Luescher, Ludwig Institute, Epalinges, Switzerland) together with 10 µg/ml of anti-CD28 (CD28.2, Immunotech).

Raji B cells were stimulated using P/I as described above. Stimulations were conducted for various time intervals, depending on the cell type, as indicated in the figures.

Lysis of Stimulated Cells and SDS-PAGE

Stimulations were stopped by addition of ice-cold Tris-NaCl buffer (20 mM Tris-HCl pH 7.4, 150 mM NaCl), and pelleted cells were lysed in Tris-NaCl lysis buffer containing 1% NP40, proteinase inhibitors (Complete, Roche) and phosphatase inhibitors (cocktails I and II, Sigma).

Postnuclear cell lysates were boiled with reducing SDS-sample buffer and analyzed on 16x20 cm gels by 15% SDS-PAGE according to Anderson, N. L. & Anderson, N. G. Analytical techniques for cell fractions. XXII. Two-dimensional analysis of serum and tissue proteins: multiple gradient-slab gel electrophoresis. Anal Biochem 85, 341-54 (1978).

Western Blots of Cell-Lysates

Primary antibodies used are monoclonal mouse anti-phospho ERK (Sigma), rabbit anti-phospho-IκBα (5A5, Cell Signalling), rabbit anti-IκBα (Sigma), and rabbit anti-Bcl10 (H-197, Santa Cruz). Western blots were revealed using HRP-coupled goat anti-mouse or anti-rabbit antibodies (Jackson Immunoresearch).

Results

The results are shown in FIGS. 1 a-c. A faster migrating Bcl10 species, that starts to appear after 15 min of stimulation (FIGS. 1, a and b) was observed.

In all Figures, black arrowheads indicate the position of unmodified Bcl10, while white arrowheads indicate a faster migrating form of Bcl10.

The appearance of this Bcl10 species was delayed with respect to IκB phosphorylation (FIG. 1a), and persisted for several hours after TCR engagement (not shown). Generation of the faster migrating Bcl10 species could also be observed in human CTL clones stimulated with anti-CD3 and anti-CD28, PMA and ionomycin or specific MHCp tetramers (FIG. 1b). Stimulation of human Raji B cells with PMA and ionomycin led to similar results (FIG. 1c).

Example 2

Relevance of Signalling Components Up-Stream Bcl10 in the NF-κB Pathway

To test the relevance of signalling components acting upstream and downstream of Bcl10 in the NF-κB pathway, and in particular the association of Bcl10 with its upstream binding partner Carma1 through a caspase recruitment domain (CARD), a number of further experiments were conducted.

Experiments

In a first approach, Jurkat cells were pre-incubated with either the pan-PKC inhibitor bisindolyl-maleimide VIII (BIM) or with Gö6976, an inhibitor of classical (Ca$_2$+- and DAG-dependent) PKC isoforms, before stimulation with CD3/CD28 as indicated in Example 1. For pre-incubation, the cells were incubated with 5 mM Gö6976 (Calbiochem) or 500 nM Bisindoleylmaleimide VIII acetate (Alexis), or solvent control for 30 min at 37° in RPMI with 0.5% serum directly prior to stimulation.

In a further approach, Jurkat cells were lentivirally transduced with Carma1-specific or control shRNA constructs as described in Rueda, D. et al. "Bcl10 controls TCR- and FcγR-induced actin polymerisation". J. Immunol. 178, 4373-4384 (2007). These cells were stimulated with CD3/CD28 or with P/I as described in Example 1.

Moreover, two types of Malt1-silenced Jurkat cells were exposed to a CD3/CD28 stimulation as described in Example 1 above. The first type (#1) was silenced by lentiviral silencing vector for Maki as described by Rueda, D. et al (see above), and the second, independent Malt1 silencing vector (#2) was obtained from OpenBiosystems (Clone TRCN0000073826).

Furthermore, Jurkat cells expressing constructs for VSV-tagged wt or CARD-mutated, dominant negative Carma1 (Carma1-DN) were prepared by retroviral transduction of Jurkat cells, as disclosed in Gaide, O. et al. "CARMA1 is a critical lipid raft-associated regulator of TCR-induced NF-kappa B activation" Nat. Immunol. 3, 836-843 (2002)). This construct has a non-functional CARD motif that does not allow binding to Bcl10 which is required for the formation of a Carma1-Bcl10-Malt1 complex (reviewed in Thome 2004, cited above). These cells were stimulated with CD3/CD28 as described in Example 1.

In another experiment, Jurkat cells were lentivirally transduced with a VSV-tagged expression construct for the Carma1 coiled coil domain (or empty vector), see also A Tanner, M. J., Hanel, W., Gaffen, S. L. & Lin, X. CARMA1 Coiled-coil domain is involved in the oligomerization and subcellular localization of CARMA1, and is required for T cell receptor-induced NF-kappa B activation. J Biol Chem (2007). This construct lacks the N-terminal CARD domain of Carma 1 as well as part of the C-terminus and prevents oligomerization of endogenous Carma1 in the cell by interfering with the oligomerization process.

Cell lysis and western blots was done as in Example 1. The primary antibody for the experiment with VSV-tagged wt or VSV-tagged Carma1-DN and Carma1-coiled-coil construct is monoclonal mouse anti-VSV (P5D4, Sigma). For Carma1, a rabbit anti-Carma1 (AL220, Alexis) antibody was used.

RESULTS & CONCLUSIONS

Figure 2:
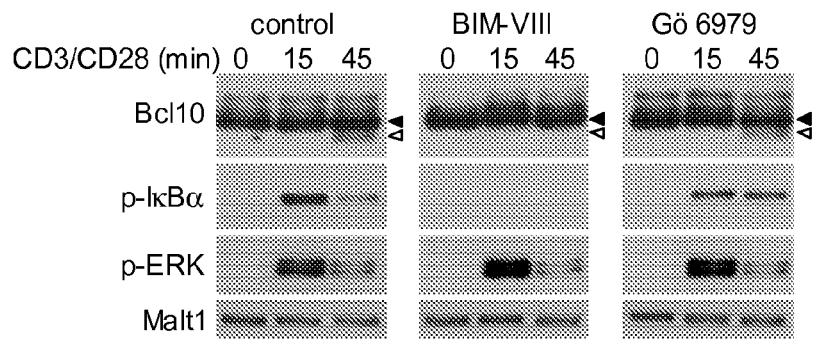
FIGS. 2 a-e show western blots of lysates of different T cell-lines as indicated following stimulation of the cells with various TCR stimulants.
Figure 2:
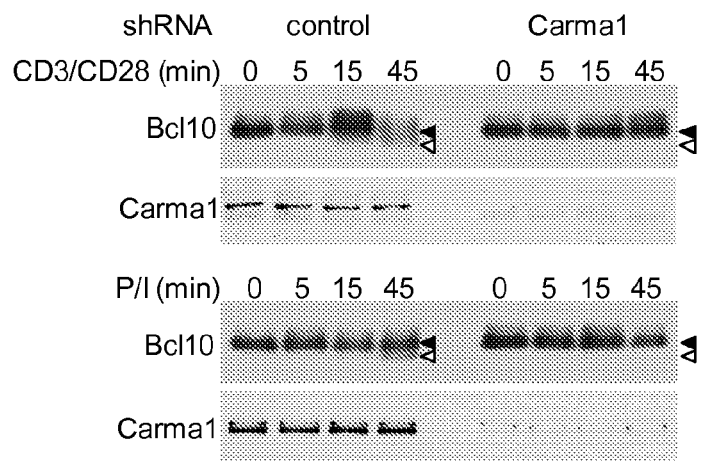
Figure 2:
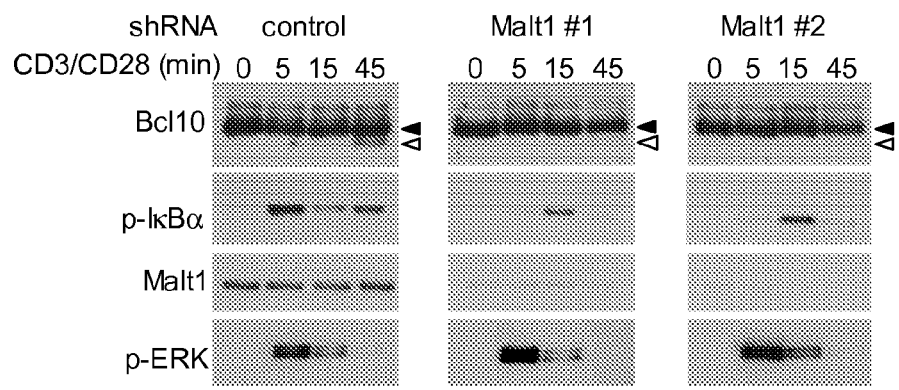
Figure 2:
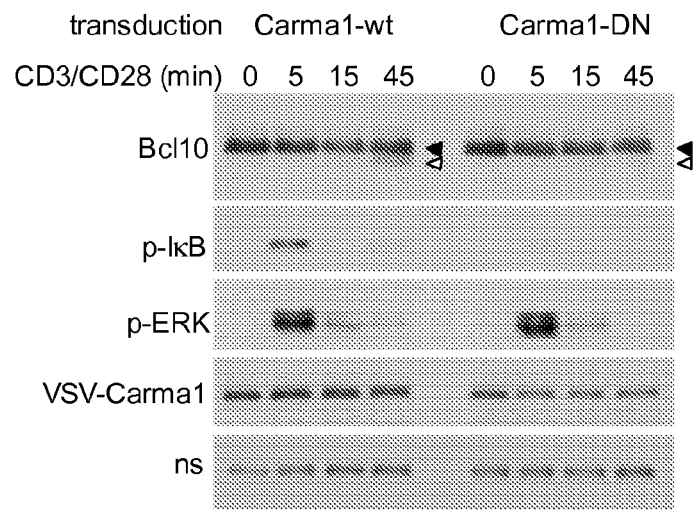
Figure 2:
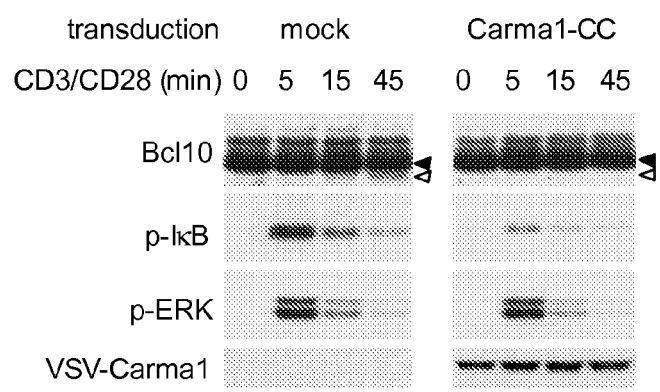

The outcome of these studies can be seen in FIGS. 2 a-d.

Consistent with a described role for PKCtheta (a $Ca^{2+}$-independent, so-called novel PKC isoform) upstream of the Carma1-Bcl10-Malt1 complex in T cells, BIM but not Gö6976 prevented the generation of the faster migrating Bcl10 species (FIG. 2a). Moreover, its generation was prevented by shRNA-mediated silencing of Carma1 (FIG. 2b) and strongly reduced by the expression of a CARD-mutated, dominant negative mutant of Carma1 that is unable to bind Bcl10 (FIG. 2e). Expression of a Carma1 coiled coil construct, which prevents Carma1 oligomerization, also had a clear inhibitory effect (FIG. 2f). Together, these findings suggest that formation of the faster migrating Bcl10 species depends on its recruitment by Carma1 and on Carma1 oligomerization. In addition, silencing of Malt1 expression by two independent shRNAs clearly impaired the generation of the observed Bcl10 modification.

Example 3

Identifying Cleavage by Malt1 after Arg228 Close to C-Terminus of Bc110

3.1 Two-D Gel Electrophoresis-Detecting Cleavage by Malt1 Close to C-Terminus of Bcl10

In order to determine if proteolytic cleavage was at the origin of the faster migrating Bcl10 species, Jurkat cells were stimulated for 30 min by PMA and ionomycin and cell extracts were prepared and analysed by two dimensional gel electrophoresis and anti-Bcl10 Western blot as described by Rueda et al. 2007, see above.

Figure 3:
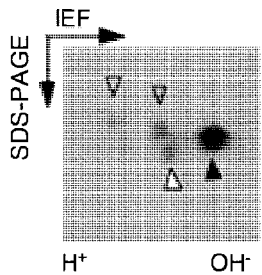
FIG. 3 a shows a western blot of Bcl10 in a 2 dimensional SDS PAGE gel, revealing the presence of a faster migrating Bcl10 species at a pI more acidic than the wildtype form of Bcl10.
Figure 3:
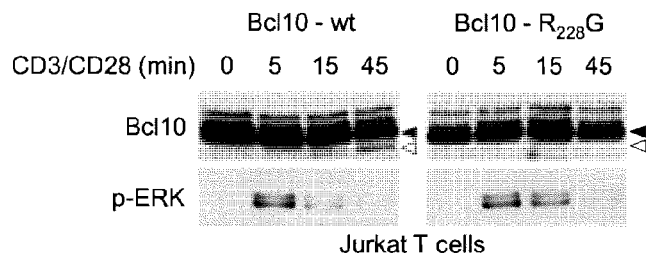
Figure 3:
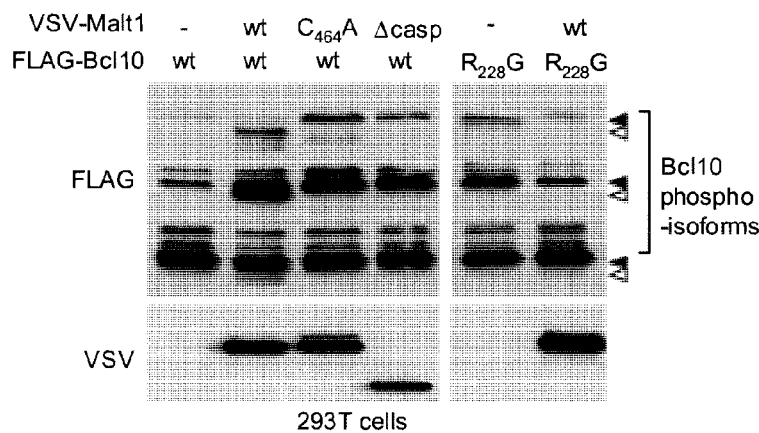

The Western blot is shown in FIG. 3a. As in FIGS. 1 and 2, the black arrowhead indicates the presence of un-phosphorylated, intact Bcl10, and the white arrowhead indicates the faster migrating species, which was detected at a pI that was more acidic than the wildtype form of Bcl10. Transparent arrowheads show two previously described phosphorylation isoforms of Bcl10 that are induced by TCR engagement (Rueda et al. 2007, see above).

The faster migrating species thus most likely resulted from proteolytic cleavage at the C-terminus of Bcl10, which contains a positively charged Arg residue (Arg 232) whose proteolytic removal could explain the more acidic pI value (FIG. 3b).

3.2 Identification of Arg228 of Bcl10 as Site of Proteolytic Cleavage

To determine whether cleavage occurred after the preceding Arg residue 228, we stably expressed a Bcl10 wt form or an Arg 228/Gly mutant in Jurkat cells and tested the effect of PMA/ionomycin stimulation on these constructs.

The Bcl10 point mutant was generated by a standard double PCR approach, subcloned into expression vectors derived from pCR3 (Invitrogen) and verified by sequencing in both directions before further subcloning into the lentiviral vector pRDI_292 (a gift of R. Iggo, ISREC, Epalinges, Switzerland) that allows expression of constructs under the EF1 promotor. The equivalent lentiviral expression vector for Bcl10 wt has been described (Rueda et al. 2007). Transduction of Jurkat T cells was performed as described before (Rueda et al. 2007).

Stimulation and Western blots were done as described in Example 1 above, using monoclonal mouse anti-FLAG (M2, Sigma).

The result is shown in FIG. 3c. It can be seen that stimulation induced the formation of a faster migrating species for the FLAG-tagged wildtype form, but not the Arg 228/Gly mutant of Bcl10, supporting the idea of a proteinase-dependent cleavage of Bcl10 after Arg 228.

3.3 Testing of Various Malt1- and Bcl10 Mutants

Human embryonic kidney cells (293T cells) were co-transfected with combinations of VSV-tagged Malt1 and FLAG-tagged Bcl10 mutant constructs that were prepared with the same method (double PCR approach, etc) as detailed above. Transfection of 293T cells was done as in Rueda et al. 2007. Transfected samples included: cells transfected with mock plasmid (devoid of functional Malt1), with VSV-Malt1 (functional wt Malt1), with VSV-Malt1 point mutated at Cys 464 (putative active site) of Malt1 (="C464/A"), and cells with VSV-Malt1 with a deletion of the caspase-like domain (aa 336 to aa 566 of Malt1) (="Δcasp") all with FLAG-tagged wt Bc110. Further cells were prepared by transfection with mock plasmid and VSV-wt Malt1, both with FLAG-tagged, point mutated Bcl10 (R228/G).

The outcome of these experiments is shown in FIG. 3d. Bcl10 cleavage was observed when wt Bcl10, but not the Arg 228/Gly mutant of Bcl10 was co-expressed with Malt1 in 293T cells, while point mutation of the neighboring residues Thr 229 and Val 230 of Bcl10 did not affect cleavage (data not shown). In this setting, Bcl10 cleavage was dependent on the presence of the intact Malt1 caspase-like domain, since deletion of this domain (deletion of aa 336 to 566) or mutation of the putative active site Cys 464 of Malt1 abolished Bcl10 cleavage.

3.4 Analysis of C-Terminal Glu-C Peptide of FLAG-Tagged Bcl10

In order to analyse the C-terminal nature of the fast and slow migrating forms of Bcl10, FLAG-tagged Bcl10 was immunoprecipitated from 293T cells co-transfected with FLAG-Bcl10 and Malt1.

In particular, pooled lysates from ten 10 cm dishes of FLAG-Bcl10- or FLAG-Bcl10- and VSV-Malt1-transfected 293T cells were used for anti-FLAG immunoprecipitation on 120 µl of anti-FLAG-agarose (Sigma). Samples were processed on 15% Anderson SDS-PAGE (Anderson et al. 1978, see above), and Coomassie-stained bands corresponding to uncleaved and cleaved Bcl10 were cut out and analyzed by in-gel Glu-C digest and mass spectrometric (MALDI-MS) analysis (TOPLAB, Munich, Germany).

Figure 4:
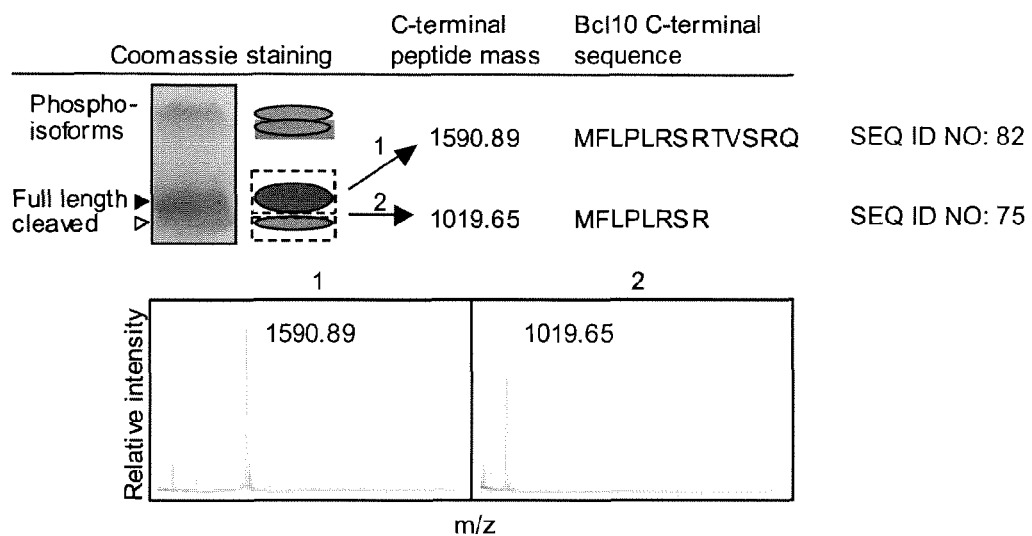
FIG. 4 shows Bcl10 C-terminal sequences of Bcl10 obtained by immunoprecipitation of FLAG-tagged Bcl10 from 293T cells cotransfected with FLAG-Bcl10 and Malt1 and digestion of isolated FLAG-Bcl10 bands by Glu-C, followed by mass spectroscopy of digests.

The results are shown in FIG. 4. Uncleaved Bcl10 contains the full length C-terminal Glu-C peptide of 1590.89 D (aa 220-233), while the sample with the Malt1-induced cleaved form of Bcl10 contains a C-terminal Glu-C peptide that stops after Arg 228, with a molecular weight of 1019.65 D (aa 220-228). This experiment confirms Arg 228 of Bcl10 as the cleavage site.

In conclusion of the experiments conducted under Example 3 Malt1 is identified as an Arg-specific protease cleaving Bcl10 after Arg 228.

3.5 Testing of Effect of Other Proteases on Bcl10 Cleavage

Figure 5:
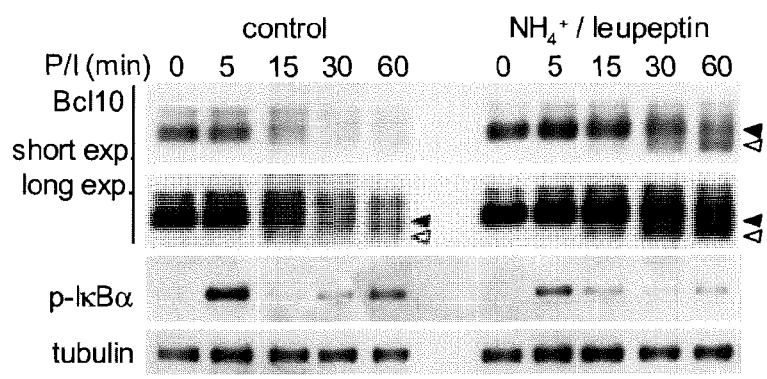
FIGS. 5 a-c show lack of an effect of various protease inhibitors targeting lysosomal proteases ($NH_4$/leupeptin), proteasomal activities (MG132) or caspases (Z-VAD-fmk) on the appearance of a faster migrating Bcl10 species.
Figure 5:
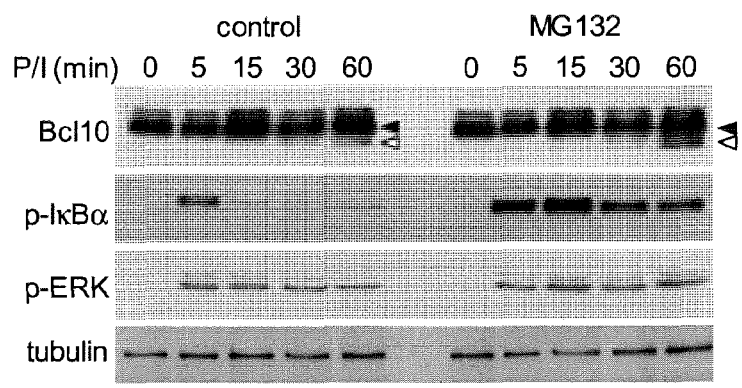
Figure 5:
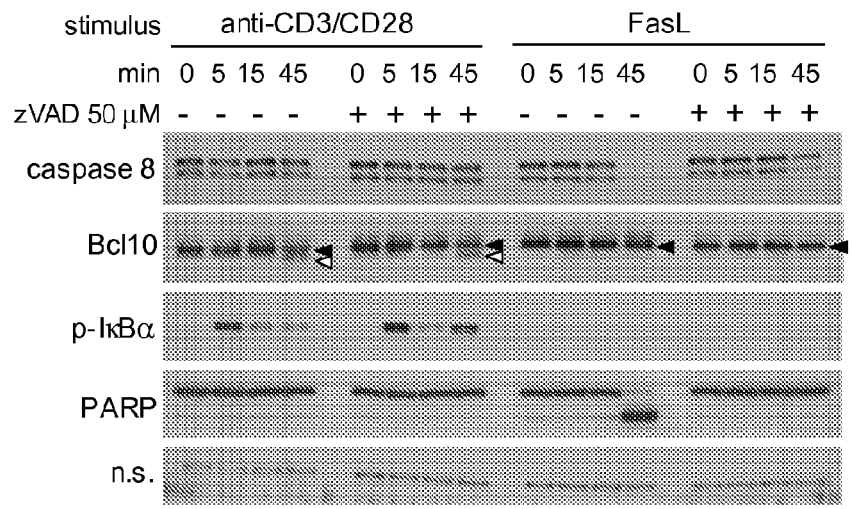

For testing if the observed proteolytic activity is an indirect effect of Malt1 on other proteases, Jurkat cells were pretreated with the lysosomal or proteasomal inhibitors ($NH_4^+$/leupeptin or MG132) or solvent control before stimulation with PMA and ionomycin, and postnuclear lysates were analyzed by Western blot as indicated. As is shown in FIG. 5a, inhibition of lysosomal proteases through pre-incubation of cells with $NH_4Cl$ and leupeptin prevented Bcl10 degradation, but did not affect generation of the faster migrating Bcl10 species corresponding to Bcl10 cleavage. Inhibition of the proteasome by MG132 also did not affect Bcl10, but efficiently stabilized P-IκB (FIG. 5b).

In an analogue experiment, Jurkat cells were pretreated with the pan-caspase inhibitor zVAD-fmk or solvent control, and stimulated with anti-CD3 and anti-CD28 antibodies or hexameric recombinant FasL for the indicated times. Post-nuclear lysates were analyzed by Western blot with the indicated primary antibodies (FIG. 5c). A non-specific band (n.s.) of the anti-Bcl10 blot served as a loading control. It can be seen from FIG. 5c that pretreatment of the cells with zVAD-fmk had no effect on anti-CD3/CD28-induced reduction in the apparent molecular weight of Bcl10, while it potently inhibited FasL-induced caspase-8 activation.

In conclusion, it is unlikely that Bcl10 cleavage is mediated by an indirect effect of Malt1 on other proteases, since inhibition of lysosomal, proteasomal or caspase-type proteolytic activities did not affect Bcl10 cleavage.

Example 4

In Vitro Protease Activity Assay

In this example, the capacity of Malt1 to cleave a Bcl10-derived fluorogenic substrate upon T-cell activation was assessed.

Unstimulated or PMA/ionomycin-stimulated Jurkat T cells were mechanically lysed in cleavage assay buffer (50 mM Tris-HCl pH 7.4, 60 mM NaCl, 100 mM $CaCl_2$ and 10 mM DTT) using a dounce homogenizer. Malt1 protease activity was determined upon addition of 50 µM Ac-LRSR-amc (amc=7-amino-4-methylcoumarin) (Peptides International, Inc.) and incubation at 30° C. for 4 h, using a Synergy microplate reader (BioTek). The experiment was repeated for various time-intervals of stimulation (0, 10, 30, 45 and 60 min). In another setting, stimulation was for 20 minutes and the cleavage of Ac-LRSR-amc (Assay time) was followed during indicated times.

Figure 6:
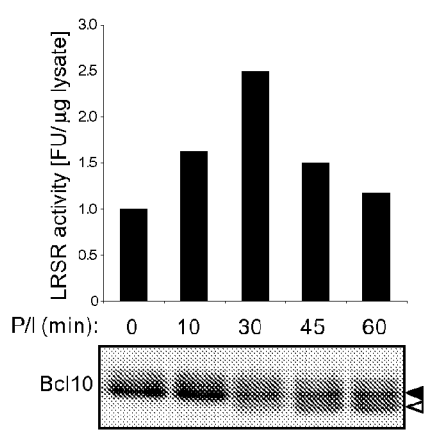
FIGS. 6 a and b show Malt1-dependent cleavage activity of lysates of T cells following T-cell activation and unstimulated control cells. For assessing cleavage activity, LRSR-peptide bound fluorogenic compound, Ac-LRSR-amc, was used.
Figure 6:
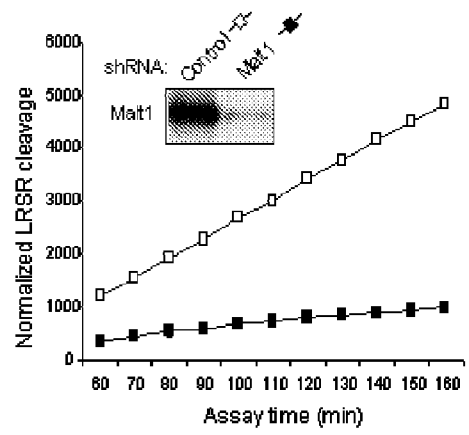

The results are shown in FIGS. 6a and 6b. As can be seen, stimulation of Jurkat cells using PMA and ionomycin led to a specific increase in proteolytic activity (FIG. 6a) that was impaired when Malt1 expression was silenced (the values in FIG. 6b are values of those samples activated for 20 min normalized to unstimulated controls). Thus, T-cell activation leads to activation of the Malt1 proteolytic activity and to a Malt1-dependent cleavage of Bcl10 after Arg 228.

Example 5

Functional Consequence of Malt1-Dependent Bcl10 Cleavage on IκB Phosphorylation

In order to assess if Malt1-mediated cleavage of Bcl10 had an influence on IκB phosphorylation, and, consequently, on NF-kB activation, the following experiment was conducted.

Jurkat cells stably transduced with wildtype Bcl10 or its Arg 228/Gly mutant (see Example 3 and FIG. 3d) were stimulated with anti-CD3 and anti-CD28 for different times (0, 5, 10, 15, 30 and 60 minutes), and cell extracts prepared as in Example 1 and analyzed by Western blot for Bcl10, P-IκB, P-ERK and P-JNK as indicated. Antibodies are as in Example 1. For P-JNK, a rabbit anti-phospho-JNK primary antibody (Biosource) was used.

It was found that intensities and kinetics of IκBα phosphorylation and degradation are similar in Jurkat cells stably expressing the wt or Arg 228/Gly form of Bcl10, indicating that the classical IκBα-dependent pathway of NF-κB activation was unaffected by Bcl10 cleavage.

Example 6

Functional Consequence of Malt1-Dependent Bcl10 Cleavage on Relative NF-κB Activity In another experiment designed to assess the influence of Malt1-mediated cleavage of Bcl10 on NF-κB response, the following experiment was conducted.

For the experiments, cells with inactive Malt 1 as described in Example 3 above were used: VSV-Malt1 (wt with functional Malt1), Δcasp, C464/A, and also another mutant, H415/A, which is mutated by a point mutation at the active site, obtained by the standard double PCR approach as described with respect to C464/A above (Example 3).

These cells were co-transfected with a renilla-luciferase and an NF-κB-firefly luciferase construct and mock plasmid to normalize transfection efficiency as disclosed by Rueda et al. (2007). Relative NF-κB activity was determined 24 h after transfection by dual luciferase assay (Rueda et al. 2007).

Figure 7:
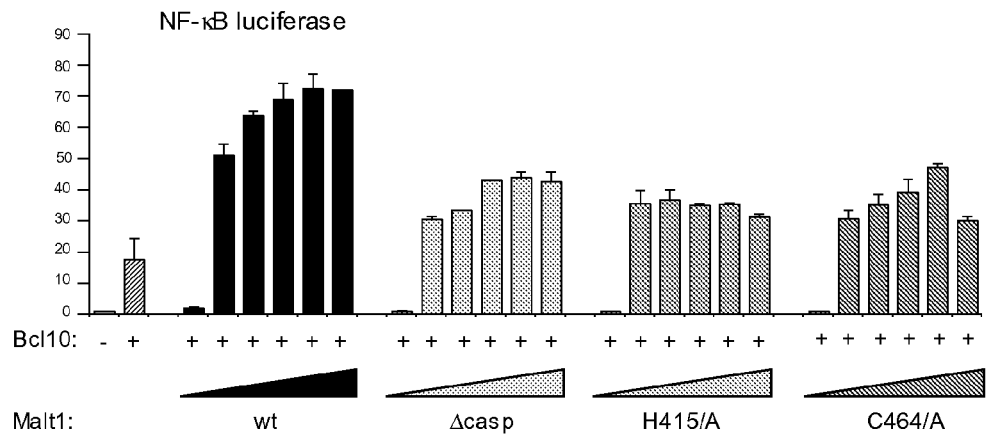
FIG. 7 shows relative NF-κB activity as determined by dual luciferase assays of 293T cells co-transfected with various Malt1 or Bcl10 expression constructs and a NF-κB-luciferase construct. Reduced NF-κB activity is found in cells with non-functional, proteolytically inactive Malt1 (Δcasp, H415/A, C464/A).

The result can be seen in FIG. 7. It can be seen that inactivation of the Malt1 catalytic activity by deletion of the caspase-like domain (Δcasp) or mutation of the active site residues Cys 464 or His 415 resulted in total NF-κB activation levels of only 50-65% of the maximum level achieved with wt Malt1. Malt1-dependent cleavage is, therefore, necessary for an optimal NF-κB response.

Example 7

Effect of Bcl10 Cleavage on T-Cell Adhesion 7.1 Adhesion Assays.

Central areas of tissue culture dishes (35-mm×10-mm) were coated for 90 min at 25° C. with 50 µl of fibronectin solution (40 µg/ml; Roche). Coated dishes were washed three times with PBS (without Ca2+ and Mg2+) and were blocked for 2 h with 1% (wt/vol) BSA in PBS. Cells were washed with Hank's balanced-salt solution (Gibco) and were left unstimulated or were stimulated at 37° C. for 30 min with $MnCl_2$ (1 mM) or PMA (100 ng/ml), or for 5 min with anti-human CD3 and anti-CD28 (see example 1). Subsequently, cell suspensions were added to fibronectin-coated tissue culture dishes followed by incubation for additional 30 min at 37° C. Non-adherent cells were removed by washing of the dishes three to five times with Hank's balanced-salt solution. Adherent cells were counted in six separate fields with a microscope with an ocular counting reticule.

7.2 Results

Figure 8:
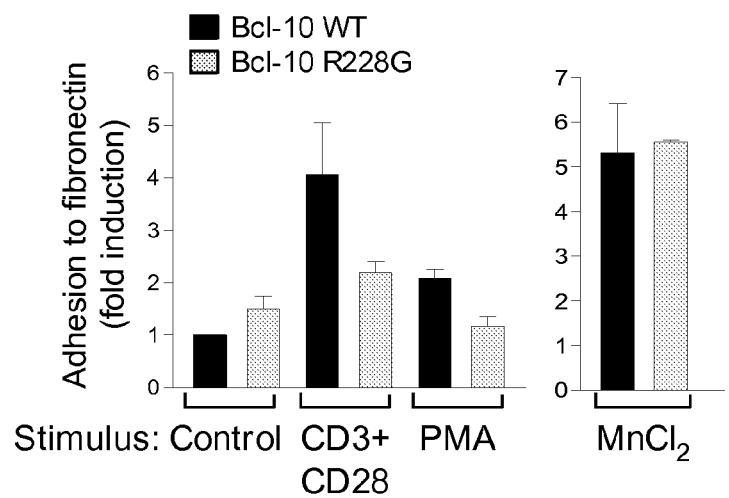
FIG. 8 shows the adhesion on fibronectin-coated culture dishes of Bcl10-silenced Jurkat T cells transduced with expression vectors for with wild-type Bcl10 or a mutant Bcl10 R228G, which cannot be cleaved by Malt1. It can be seen that cells expressing wildtype Bcl10, stimulated with anti-human CD3 and anti-CD28 or with PMA, show better adherence to fibronectin than Bcl10 R228G mutants. These results show the implication of hMalt1-mediated enzymatic cleavage of Bcl10 for the adhesion of activated T cells.

After activation with either anti-CD3 and anti-CD28 or PMA, cells expressing the R228G mutant had less adhesion to fibronectin than did cells expressing wild-type Bcl-10 (FIG. 8). In contrast, manganese-induced adhesion was similar in cells expressing wild-type Bcl-10 or the R228G mutant (FIG. 8).

Example 8

Detection of Cleaved Bcl10 in B-Cell Lymphomas

In order to know whether the cleaved form of Bcl10 is detectable in B-cell lymphomas samples from biopsies were taken and analysed as follows: Lymphoma samples from lymph node, spleen and gastrointestinal biopsies from patients with mucosa-associated lymphoid tissue (MALT) lymphoma, diffuse large B-cell lymphoma (DLBCL), mantle cell lymphoma (MCL) or follicular cell lymphoma (FCL) were immediately frozen without additives and stored for 3-24 months before lysis. Cells were lysed in 50 mM Hepes pH 7.6, 4 mM EDTA, 150 mM NaCl und 1% Triton X-100 supplemented with the following proteinase and phosphatase inhibitors: 2 mM PMSF, 2 µg/ml aprotinin and 5 µg/ml leupeptin, 2 mM $Na_3VO_4$, 100 mM NaF und 50 mM $Na_4P_2O_7$. Lysates were stored at −80° C. before analysis by SDS-PAGE and Western blot. Controls include lysates of non-stimulated (−) and PMA/ionomycin-stimulated (+) $CD8^+$ T cell clones.

The result can be seen in FIG. 9. Bcl10 cleavage was clearly detectable in two samples of MALT lymphomas characterized by the t(11;18) translocation which leads to cJAP2-Malt1 fusion proteins with strong NF-κB activating capacity. Moreover, Bcl10 cleavage was detectable in 11 out of 12 additional lymphoma samples tested, suggesting that Bcl10 cleavage might be a frequent and relevant event in the pathogenesis of B-cell lymphomas.

Example 9

Inhibition of the Proteolytic Activity of Malt1 by Small Peptide Inhibitors

To test the efficiency of inhibitors, Jurkat T cells stimulated or not with PMA and ionomycin for 20 min are mechanically lysed in cleavage assay buffer (see example 4) in the absence or presence of increasing concentrations of a irreversble cell permeable inhibitor peptide (z-VRPR-fmk). This inhibitor was designed based on an optimal substrate cleavage sequence reported for the plant metacaspase AtMC9 (see ref. by Vercammen et al. 2006, J. Mol. Biol., 364(4):625-36). Malt1 protease activity is determined as described in example 4. To test the efficiency of the peptide inhibitor on living cells, Jurkat T cells or human primary cytolytic T cells (CTLs) are pre-incubated for 1 h with indicated concentrations of z-VRPR-fmk (see above), before stimulation with PMA and ionomycin for 20 min, lysis of the cells and detection of Bcl10 cleavage by Western blot (see example 1). Moreover, experiments are performed to assess the effect of the inhibitor on anti-CD3/CD28-induced NF-κB activation in Jurkat T cells, on IL-2 production of Jurkat cells stimulated by incubation with antigen-presenting cells (Raji cells in combination with the superantigen SEE) and on stimulation-induced adhesion to fibronectin (see example 7)).

In the presence of the inhibitor peptide, we observe a reduction of the activation-induced LRSR-amc cleavage activity (FIG. 11a) and the activation-induced cleavage of Bcl10 (FIGS. 11, b and c). Moreover, the inhibitor impairs the capacity of T cells to activate NF-κB, to produce IL-2 and to adhere to fibronectin upon T-cell activation (FIGS. 11, d-f). This suggests that small peptide inhibitors with homology to the Malt1 recognition sequence can be used to inhibit Malt activity in vitro and in living cells.

Example 10

Detection of Malt1-Specific Cleavage with a Cleavage-Specific Anti-Bcl10 Antibody Antibodies that exclusively recognize the cleaved form of Bcl10 were produced. To generate these antibodies, a rabbit was immunized with a short peptide comprising the 8 amino acids aminoterminal to the cleavage site (the peptide sequence is MFLPLRSR (SEQ ID NO: 75)). The peptide was coupled to the carrier protein KLH and used for repeated immunization of a rabbit. Peptide synthesis, coupling to the carrier and immunization were performed by Eurogentech according to standard procedures. The affinity and/or specificity of the antibodies contained in the serum was further increased by affinity-purification over a CNBr-Sepharose column to which the peptide used for immunization was covalently bound.

Figure 12:
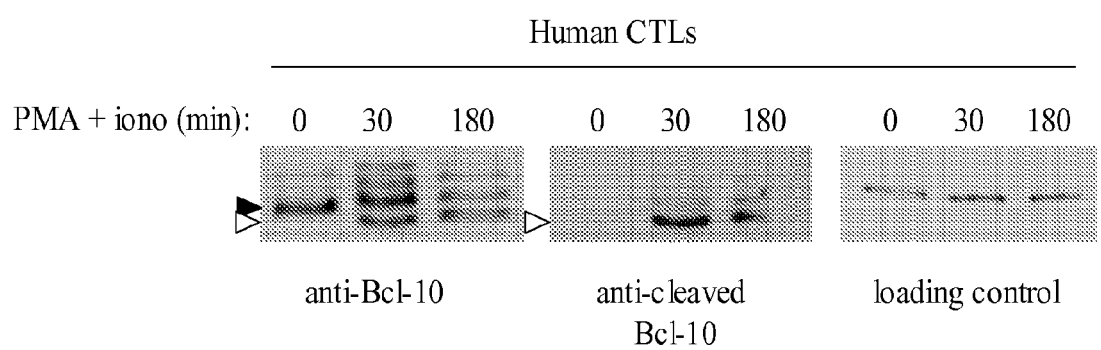
FIG. 12 shows immunoblot analysis of lysates of human cytotoxic T lymphocytes (CTLs) that were left unstimulated or stimulated for the indicated times with the phorbolester PMA and ionomycin. The anti-Bcl10 blot (left panel) detects Bcl10 (black arrowhead), cleaved Bcl10 (white arrowhead) and phosphorylated isoforms of Bcl10 with a higher apparent molecular weight. The antibodies specific for cleaved Bcl10 (middle panel) detect cleaved Bcl10 (and higher migrating phosphorylated isoforms of cleaved Bcl10) in samples of stimulated cells, but does not cross-react with uncleaved Bcl10, since it does not detect Bcl10 in lysates of unstimulated cells.

In the experiment shown in FIG. 12, the affinity-purified antibodies were used to assess the presence of cleaved Bcl10 in lysates of human cytotoxic T lymphocytes (CTL) that were either left unstimulated or stimulated for the indicated times with PMA and ionomycin, as described above. Proteins contained in the lysates were separated electrophoretically and transferred to nitrocellulose. Samples were analysed by Western blot using a commercially available anti-Bcl10 antibody (left panel in FIG. 12), the affinity-purified anti-cleaved Bcl10 antibodies (middle panel) or an irrelevant antibody to demonstrate equivalent protein content of samples (right panel). The anti-Bcl10 antibody detects Bcl10 in all samples, and stimulation-induced phosphorylation isoforms of Bcl10 that are present predominantly in the lysates of activated cells. In contrast, the anti-cleaved Bcl10 antibodies detect only the cleaved (unphosphorylated and phosphorylated) forms of Bcl10, which are present in stimulated cells, but absent from unstimulated cells.

Antibodies as produced in this example are useful for the specific detection of Bcl10 cleavage, which serves as a readout for MALT1 activity, for purposes of research, drug development and diagnosis. With such antibodies, cleaved Bcl10 can for example be specifically detected in samples of lysates of lymphocytes that have been stimulated to mimic T-cell activation (see FIG. 12). Furthermore, such antibodies can be used in a quantitative immunoassay to detect cleaved BCL10 in cell lysates. Such an assay, for example an ELISA assay, could be performed with lysates of cells that were pre-incubated, before stimulation, with compounds acting as Malt1 inhibitors, and thus serve as a screening assay for therapeutically useful Malt1 inhibitors. Another interesting application of antibodies specific for cleaved Bcl10 could be their use in a immunohistochemistry-based assay to diagnose the status of Malt1 activation in suitable cells or tissue samples obtained from patients suffering for example from lymphoma, auto-immune disease or inflammatory conditions.

OVERALL CONCLUSION

The examples demonstrate that Malt1 has arginine-directed proteolytic activity and that an increase in this activity is specifically induced by T-cell activation. A C-terminal $LRSR_{228}$ motif at the C-terminus of Bcl10 was identified as a Malt1 target sequence. Malt1-dependent Bcl10 cleavage is crucial for T-cell activation, since mutation of the Bcl10 cleavage site prevents Malt1-dependent Bcl10 processing and results in impaired TCR-induced T-cell adhesion. Moreover, inhibition of the proteolytic activity of Malt1 using a Malt1 inhibitor impairs various parameters of T-cell activation, including NF-κB activation, IL-2 production and T-cell adhesion. Importantly, processed Bcl10 is also detectable in various forms of B-cell lymphoma. Thus, Malt1 is essential for lymphocyte activation by cleavage of Bcl10 and of additional protein substrates, and therefore represents an interesting target of immunomodulatory drug development.

The invention claimed is:

1. An in vitro method of screening for a bioactive compound exerting an inhibitory effect on a proteolytic activity of Malt1, the method comprising the steps:
   1) exposing and/or contacting a compound to be screened to an oligomerized polypeptide having at least 50% sequence identity with SEQ. ID. NO. 48 and/or comprising the caspase-like domain of Malt1, the caspase-like domain being amino acids 336-572 of SEQ. ID. NO. 48, and the oligomerized polypeptide has Malt1-specific proteolytic activity, said oligomerized polypeptide being selected from a sample of cells comprising said oligomerized polypeptide, a sample of destroyed cells comprising said oligomerized polypeptide, and from recombinant, purified oligomerized polypeptide;
   2) adding a marker peptide substrate, wherein said marker peptide substrate is susceptible of proteolytic cleavage by Malt1;
   3) assessing Malt1-specific proteolytic activity by assessing the consumption of said marker peptide substrate when cleaved by said oligomerized polypeptide and/or assessing the presence of cleaved marker peptide substrate; and
   4) selecting said compound of step 1 if said compound inhibits said proteolytic activity.

2. The method of claim 1, wherein said bioactive compound is effective in the prevention or treatment of lymphomas.

3. The method of claim 1, wherein said marker peptide substrate comprises a peptide comprising an amino acid sequence selected from the group consisting of SEQ ID NO: 4 to SEQ ID NO: 47, wherein an arginine residue of said sequence is present at the C-terminal end of said sequence, and wherein said marker peptide substrate is cleaved following the carboxyl terminus of said arginine residue by said proteolytic activity.

4. The method of claim 1, wherein said marker peptide substrate comprises a peptide comprising an amino acid sequence selected from the group consisting of SEQ ID NO: 4 to SEQ ID NO: 47, wherein an arginine residue is present at the C-terminal end of said sequence, wherein the N-terminus of said peptide is further modified by a chemical group selected from the group consisting of H, Acetyl, and benzyloxycarbonyl.

5. The method of claim 1, further comprising the step of contacting said oligomerized polypeptide with a compound comprising an amino acid sequence selected from the group consisting of SEQ ID NO: 4 to SEQ ID NO: 47, wherein an arginine residue of said sequence is present at the C-terminal end of said sequence, said sequence being linked at said C-terminal end to a functional group selected from the group consisting of chloromethylketone, fluoromethylketone and aldehyde, and said amino acid sequence being optionally further substituted.

6. The method of claim 1, further comprising the step of contacting said oligomerized polypeptide with a compound of formula z-VRPR-fmk, wherein VRPR is SEQ ID NO: 65, z is benzyloxycarbonyl and fmk is fluoromethylketone.

7. The method of claim 4, wherein said marker peptide is further modified by biotinyl, by alkylation with C1-C5 alkyl of the amino group of arginine residues of the peptide and/or by a fluorescent grouping.

8. The method of claim 1, wherein said oligomerized polypeptide is recombinant and purified oligomerized polypeptide.

9. The method of claim 1, wherein assessing Malt1-specific proteolytic cleavage is the qualitative finding of presence or absence of said proteolytic activity.

10. The method of claim 1, wherein said marker peptide substrate is a compound which, when cleaved, loses or obtains a measurable chemical, physical and/or biological property, said property depending on the close physical proximity or on the absence of such proximity, respectively, of two parts of the substrate that precede and follow a cleavage site and which physical proximity or absence of proximity is thus lost or obtained, respectively, by said Malt-1 specific proteolytic activity.

11. The method of claim 1, wherein said marker peptide substrate is a chemically modified peptide compound.

12. The method of claim 1, wherein assessing Malt1-specific proteolytic activity is the quantitative approximation of such proteolytic activity.

* * * * *